US010130660B2

(12) United States Patent
Park et al.

(10) Patent No.: US 10,130,660 B2
(45) Date of Patent: Nov. 20, 2018

(54) PERIPHERAL BLOOD STEM CELLS WITH IMPROVED ANGIOGENIC PROPERTIES AND USE THEREOF

(71) Applicant: SEOUL NATIONAL UNIVERSITY R&DB FOUNDATION, Seoul (KR)

(72) Inventors: Young-Bae Park, Seoul (KR); Hyo-Soo Kim, Seoul (KR); Hyun-Jae Kang, Seoul (KR); Jin Hur, Seoul (KR); Jeehoon Kang, Seoul (KR); Jung-Kyu Han, Anyang-si (KR); Ji-Yeon Yun, Goyang-si (KR); Jae-Il Choi, Seoul (KR); Jin-A Kang, Incheon (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 14/896,336

(22) PCT Filed: Jun. 5, 2014

(86) PCT No.: PCT/KR2014/004985
§ 371 (c)(1),
(2) Date: Dec. 4, 2015

(87) PCT Pub. No.: WO2014/196815
PCT Pub. Date: Dec. 11, 2014

(65) Prior Publication Data
US 2016/0151419 A1 Jun. 2, 2016

(30) Foreign Application Priority Data

Jun. 5, 2013 (KR) .................. 10-2013-0064833
Jun. 5, 2014 (KR) .................. 10-2014-0068116

(51) Int. Cl.
A61K 35/28 (2015.01)
A61K 35/12 (2015.01)
C12N 5/0789 (2010.01)
C12N 5/078 (2010.01)

(52) U.S. Cl.
CPC ............ *A61K 35/28* (2013.01); *C12N 5/0634* (2013.01); *C12N 5/0647* (2013.01); *A61K 2035/124* (2013.01); *C12N 2501/14* (2013.01); *C12N 2501/22* (2013.01); *C12N 2506/11* (2013.01)

(58) Field of Classification Search
None
See application file for complete search history.

(56) References Cited

U.S. PATENT DOCUMENTS

2006/0205071 A1 9/2006 Hasson et al.
2007/0281352 A1 12/2007 Dietz et al.
2009/0280094 A1 11/2009 Matsumoto et al.
2009/0291061 A1 11/2009 Riordan et al.

FOREIGN PATENT DOCUMENTS

KR 10-2007-0054140 A 5/2007
WO 2008/048671 A1 4/2008

OTHER PUBLICATIONS

Heeschen et al, Blood, 2003, vol. 102, p. 1340-1346.*
Kanabara et al., Ann. Vasc. Dis., 2012, vol. 5, No. 1, p. 52-60.*
Kang et al., Circulation, 2006, vol. 114 suppl I, p. I-145-I-151.*
Hirata et al., Journal of American College of Cardiology, 2006, vol. 48, No. 1, p. 176-184.*
Lane et al., Blood, 1995, vol. 85, No. 1, p. 275-282.*
Joshi et al., "Immunological Properties of Mononuclear Cells from Blood Stem Cell Harvests Following Mobilization with Erythropoietin + G-CSF in Cancer Patients", Cytotheraphy, 2000, vol. 2, No. 1, pp. 15-24.
Extended European Search Report dated Jan. 18, 2017 of corresponding European Application No. 14807410.7—8 pages.
Wei et al., "Effects of JAK2-dependent ERK signal pathway on erythropoietin-induced functional activation of bone marrow-derived endothelial progenitor cells", Journal of Clinical Rehabilitative Tissue Engineering Research, Dec. 3, 2010, vol. 14, No. 49, pp. 9203-9207.
Office Action dated Jun. 14, 2017 in corresponding Chinese Patent Application No. 201480032228.7—2 pages.
Kim et al., "Priming with Angiopoietin-1 Augments the Vasculogenic Potential of the Peripheral Blood Stem Cells Mobilized with Granulocyte Colony-Stimulating Factor Through a Novel Tie2/Ets-1 Pathway", Circulation, Nov. 2009, vol. 120, No. 22, pp. 2240-2250.
Santoso et al., "Safety and Feasibility of Combined Granulocyte Colony Stimulating Factor and Erythropoetin Based-Stem Cell Therapy Using Intracoronary Infusion of Peripheral Blood Stem Cells in Patients with Recent Anterior Myocardial Infarction: One-Year Follow-up of A Phase 1 Study", Acta Med. Inndones., Apr. 2011, vol. 43, No. 2, pp. 112-121.
Spaan et al., "Erythropoietin administration suppresses human monocyte function in vitro and during therapy-induced anemia in HCV patients", Antiviral Research, Jun. 2013, vol. 98, No. 3, pp. 469-475.
International Search Report dated Oct. 27, 2014 of PCT/KR2014/004985 which is the parent application and its English translation—6 pages.

* cited by examiner

*Primary Examiner* — Kade Ariani
(74) *Attorney, Agent, or Firm* — Knobbe Martens Olson & Bear LLP

(57) ABSTRACT

The present application discloses a method for producing peripheral blood stem cells with improved angiogenic properties through EPO or APS priming, and a use thereof. The cells produced according to the method of the present application induce angiogenesis, and thus can be effectively used for the regeneration of, or recovery from, various diseases requiring facilitation of angiogenesis, such as ischemic diseases occurring in the muscle, brain, heart, kidney, or large intestine, e.g. tissue damage, cerebral infarction, stroke, reperfusion injury, myocardial infarction, congestive heart failure, peripheral vascular obstruction, cardiac hypertrophy, low heart contraction, low heart dilatation, maladaptive cardiomegaly, systolic heart failure, diastolic heart failure, hypertensive heart failure, artery or mitral valve diseases, heart blood vessels with pulmonary valve diseases, or ischemic heart blood vessels, caused by ischemia.

13 Claims, 29 Drawing Sheets
Specification includes a Sequence Listing.

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: IL-8 forward primer

<400> SEQUENCE: 1
gtgcagtttt gccaaggagt                                              20

<210> SEQ ID NO 2
<211> LENGTH: 20
<212> TYPE: DNA
<213> ORGANISM: Artificial Sequence
<220> FEATURE:
<223> OTHER INFORMATION: IL-8 reverse primer

<400> SEQUENCE: 2
aatttctgtg ttggcgcagt                                              20

<210> SEQ ID NO 3
<211> LENGTH: 20
<212> TYPE: DNA
<213> ORGANISM: Artificial Sequence
<220> FEATURE:
<223> OTHER INFORMATION: IL-10 forward primer

<400> SEQUENCE: 3
gcctaacatg cttcgagatc                                              20

<210> SEQ ID NO 4
<211> LENGTH: 20
<212> TYPE: DNA
<213> ORGANISM: Artificial Sequence
<220> FEATURE:
<223> OTHER INFORMATION: IL-10 reverse primer

<400> SEQUENCE: 4
tgatgtctgg gtcttggttc                                              20

<210> SEQ ID NO 5
<211> LENGTH: 24
<212> TYPE: DNA
<213> ORGANISM: Artificial Sequence
<220> FEATURE:
<223> OTHER INFORMATION: bFGF forward primer

<400> SEQUENCE: 5
ggctatgaag gaagatggaa gatt                                         24

<210> SEQ ID NO 6
<211> LENGTH: 24
<212> TYPE: DNA
<213> ORGANISM: Artificial Sequence
<220> FEATURE:
<223> OTHER INFORMATION: bFGF reverse primer

<400> SEQUENCE: 6
tgccacatac caactggtgt attt                                         24

<210> SEQ ID NO 7
<211> LENGTH: 22
<212> TYPE: DNA
<213> ORGANISM: Artificial Sequence

```
<220> FEATURE:
<223> OTHER INFORMATION: MMP9 forward primer

<400> SEQUENCE: 7
gggcttagat cattcctcag tg                                            22

<210> SEQ ID NO 8
<211> LENGTH: 20
<212> TYPE: DNA
<213> ORGANISM: Artificial Sequence
<220> FEATURE:
<223> OTHER INFORMATION: MMP9 reverse primer

<400> SEQUENCE: 8
gccattcacg tcgtcettat                                               20

<210> SEQ ID NO 9
<211> LENGTH: 23
<212> TYPE: DNA
<213> ORGANISM: Artificial Sequence
<220> FEATURE:
<223> OTHER INFORMATION: Integrin alphaV forward primer

<400> SEQUENCE: 9
aatcttccaa ttgaggatat cac                                           23

<210> SEQ ID NO 10
<211> LENGTH: 21
<212> TYPE: DNA
<213> ORGANISM: Artificial Sequence
<220> FEATURE:
<223> OTHER INFORMATION: Integrin alphaV reverse primer

<400> SEQUENCE: 10
aaaacagcca gtagcaacaa t                                             21

<210> SEQ ID NO 11
<211> LENGTH: 22
<212> TYPE: DNA
<213> ORGANISM: Artificial Sequence
<220> FEATURE:
<223> OTHER INFORMATION: Integrin beta8 forward primer

<400> SEQUENCE: 11
aatttggtag tggaagccta tc                                            22

<210> SEQ ID NO 12
<211> LENGTH: 20
<212> TYPE: DNA
<213> ORGANISM: Artificial Sequence
<220> FEATURE:
<223> OTHER INFORMATION: Integrin beta8 reverse primer

<400> SEQUENCE: 12
gtcacgtttc tgcatccttc                                               20

<210> SEQ ID NO 13
<211> LENGTH: 20
<212> TYPE: DNA
<213> ORGANISM: Artificial Sequence
<220> FEATURE:
<223> OTHER INFORMATION: IL8 forward primer

<400> SEQUENCE: 13
ggccgtggct ctcttggcag                                               20
```

```
<210> SEQ ID NO 14
<211> LENGTH: 20
<212> TYPE: DNA
<213> ORGANISM: Artificial Sequence
<220> FEATURE:
<223> OTHER INFORMATION: IL8 reverse primer

<400> SEQUENCE: 14
tgtgttggcg cagtgtggtc                                                    20

<210> SEQ ID NO 15
<211> LENGTH: 20
<212> TYPE: DNA
<213> ORGANISM: Artificial Sequence
<220> FEATURE:
<223> OTHER INFORMATION: IL13 forward primer

<400> SEQUENCE: 15
tagggagggg taaaattcct                                                    20

<210> SEQ ID NO 16
<211> LENGTH: 20
<212> TYPE: DNA
<213> ORGANISM: Artificial Sequence
<220> FEATURE:
<223> OTHER INFORMATION: IL13 reverse primer

<400> SEQUENCE: 16
cggtgacaaa cacactcatt                                                    20

<210> SEQ ID NO 17
<211> LENGTH: 23
<212> TYPE: DNA
<213> ORGANISM: Artificial Sequence
<220> FEATURE:
<223> OTHER INFORMATION: IL17A forward primer

<400> SEQUENCE: 17
gacctcattg gtgtcactgc tac                                                23

<210> SEQ ID NO 18
<211> LENGTH: 23
<212> TYPE: DNA
<213> ORGANISM: Artificial Sequence
<220> FEATURE:
<223> OTHER INFORMATION: IL17A reverse primer

<400> SEQUENCE: 18
ggacagagtt catgtggtag tcc                                                23

<210> SEQ ID NO 19
<211> LENGTH: 20
<212> TYPE: DNA
<213> ORGANISM: Artificial Sequence
<220> FEATURE:
<223> OTHER INFORMATION: bFGF forward primer

<400> SEQUENCE: 19
tcttcaacac cgaaatgctg                                                    20

<210> SEQ ID NO 20
<211> LENGTH: 20
<212> TYPE: DNA
<213> ORGANISM: Artificial Sequence
<220> FEATURE:
<223> OTHER INFORMATION: bFGF reverse primer
```

```
<400> SEQUENCE: 20
agcccagtta gagggaccat                                              20

<210> SEQ ID NO 21
<211> LENGTH: 20
<212> TYPE: DNA
<213> ORGANISM: Artificial Sequence
<220> FEATURE:
<223> OTHER INFORMATION: TNFa forward primer

<400> SEQUENCE: 21
ccctgaaaac aaccctcaga                                              20

<210> SEQ ID NO 22
<211> LENGTH: 20
<212> TYPE: DNA
<213> ORGANISM: Artificial Sequence
<220> FEATURE:
<223> OTHER INFORMATION: TNFa reverse primer

<400> SEQUENCE: 22
aagaggctga ggaacaagca                                              20

<210> SEQ ID NO 23
<211> LENGTH: 24
<212> TYPE: DNA
<213> ORGANISM: Artificial Sequence
<220> FEATURE:
<223> OTHER INFORMATION: iNOS forward primer

<400> SEQUENCE: 23
catcaacaac aatgtggaga aagc                                         24

<210> SEQ ID NO 24
<211> LENGTH: 24
<212> TYPE: DNA
<213> ORGANISM: Artificial Sequence
<220> FEATURE:
<223> OTHER INFORMATION: iNOS reverse primer

<400> SEQUENCE: 24
tggttgacaa attcgatagc ttga                                         24

<210> SEQ ID NO 25
<211> LENGTH: 23
<212> TYPE: DNA
<213> ORGANISM: Artificial Sequence
<220> FEATURE:
<223> OTHER INFORMATION: EPOR forward primer

<400> SEQUENCE: 25
gagatgccag agtcagatac cac                                          23

<210> SEQ ID NO 26
<211> LENGTH: 23
<212> TYPE: DNA
<213> ORGANISM: Artificial Sequence
<220> FEATURE:
<223> OTHER INFORMATION: EPOR reverse primer

<400> SEQUENCE: 26
aggataccta tctggtgctg gac                                          23

<210> SEQ ID NO 27
```

```
<211> LENGTH: 23
<212> TYPE: DNA
<213> ORGANISM: Artificial Sequence
<220> FEATURE:
<223> OTHER INFORMATION: CXCR4 forward primer

<400> SEQUENCE: 27
agtcaacctc tacagcagtg tcc                                              23

<210> SEQ ID NO 28
<211> LENGTH: 23
<212> TYPE: DNA
<213> ORGANISM: Artificial Sequence
<220> FEATURE:
<223> OTHER INFORMATION: CXCR4 reverse primer

<400> SEQUENCE: 28
caggatgagg atgactgtgg tct                                              23

<210> SEQ ID NO 29
<211> LENGTH: 24
<212> TYPE: DNA
<213> ORGANISM: Artificial Sequence
<220> FEATURE:
<223> OTHER INFORMATION: GAPDH forward primer

<400> SEQUENCE: 29
gggtgtgaac catgagaagt atga                                             24

<210> SEQ ID NO 30
<211> LENGTH: 25
<212> TYPE: DNA
<213> ORGANISM: Artificial Sequence
<220> FEATURE:
<223> OTHER INFORMATION: GAPDH reverse primer

<400> SEQUENCE: 30
catatttggc aggtttttct agacg                                            25
```

PERIPHERAL BLOOD STEM CELLS WITH IMPROVED ANGIOGENIC PROPERTIES AND USE THEREOF

TECHNICAL FIELD

The present application relates to a cell whose ability can be enhanced through an in-vitro priming process of a peripheral blood stem cell that is mobilized by a cytokine to be used for a disease that requires blood vessel formation, and to the field of cell therapy products that uses the same.

BACKGROUND ART

Cell therapy methods mostly use adult stem cells or progenitor cells, both of which are capable of tissue regeneration, and examples of the methods include the attempts to regenerate blood vessels and muscles by using myeloid-derived stem cells. However, the method of selecting stem cells that are suitable for the regeneration of cells and tissues as constituents of adult stem cells has not been sufficiently understood, and thus, there have been difficulties in the actual use of such a method.

Despite continuous research on cell therapy, there have always been problems of an absolute insufficiency in the number of stem cells, a low survival rate of stem cells and the like. Therefore, continuous effort is required for effective clinical applications and the maximization of efficiency in cell therapy.

Research is practically in progress on the use of drugs—which can prevent cell death—for stem cells to minimize the loss of stem cells, on inducing stem cells into other types of cells that are more suitable for tissue regeneration, and the like.

Ischemia refers to the state of an insufficient supply of blood to a particular tissue, leading to an insufficient supply of oxygen and nutrients and removal of harmful metabolites, finally bringing about tissue damage. Examples of clinically representative diseases include ischemic cardiovascular diseases. An example of a treatment for such an ischemic cardiovascular disease includes coronary artery angioplasty, but, despite continuous development of stenting technology, it is still not sufficient to restore tissues that are already damaged.

Hence, a treatment that is in the limelight is the use of stem cells in regeneration of a heart muscle.

Korean Unexamined Patent Application Publication No. 2007-0054140 relates to cord blood-derived multipotent stem cells and cell therapy products that contains the stem cells for the treatment of an ischemic necrosis disease, and it provides a cell therapy product for treating an ischemic necrosis disease, which is caused by an atherosclerotic artery disease.

Continuous development of a cell therapy product is required for the radical treatment of ischemia-related diseases.

DISCLOSURE

Technical Problem

The present application is intended to provide a cell therapy product for diseases that require blood vessel formation.

Technical Solution

In one aspect, the present application relates to a method of producing mobilized peripheral blood stem cells (mobPBSC) with improved properties of blood vessel formation, where the method includes providing a human-derived peripheral blood that is treated with a cytokine; separating a layer of mononuclear cells from the above blood; and treating the above mononuclear cells with an erythropoietin (EPO) or an activated platelet supernatant (APS).

The peripheral blood stem cell of the present application is an autologous, allogenic or xenogenic cell, and, it is particularly an autologous cell.

In another aspect, the present application also provides mobPBSC, which have improved properties of blood vessel formation and are prepared by the method of the present application.

In another aspect, the present application also relates to mobPBSC, which have improved properties of blood vessel formation and are activated by an EPO or an APS.

In the present application, a cell that is treated with an EPO has, compared to an untreated cell, increased dual expression of integrin beta-1 and -2 and of CD14/CD16, and increased expression of IL8, IL10 and FGF genes and proteins that migrated through an EPO receptor. Also, a cell that is treated with an APS has, compared to an untreated cell, increased gene expression of IL9, IL17, PDGF and VEGF, increased expression of an EPO receptor, CD34, CD31, Tie2, CXCR4, integrin alpha-5, integrin beta-1 and integrin beta-2, and increased dual expression of CD14/CD16.

The present application also provides a composition for the treatment of an ischemic disease and contains the mobPBSC of the present application. The composition can be effectively used in the treatment of an ischemic heart disease. Examples of an ischemic heart disease include myocardial infarction, angina, congestive heart failure, peripheral vascular obstruction, cardiac hypertrophy, low heart contraction, low heart dilatation, maladaptive cardiomegaly, systolic heart failure, diastolic heart failure, and hypertensive heart failure.

The cell of the present application has improved properties of blood vessel formation, and it relates to a composition intended for the facilitation of blood vessel formation and contains mobPBSC.

In another aspect, the present application also relates to a method of treating an ischemic disease that includes administering a cell that is prepared according to the present application or a composition that contains the cell to a subject that requires the treatment of the ischemic disease.

Ischemic diseases for which the treatment of the present application can be used are as mentioned above.

Advantageous Effects

The APS- or EPO-primed mobPBSC of the present application induce vasculogenesis; therefore, they can be used for various diseases that require the facilitation of blood vessel formation (e.g. ischemic diseases occurring in a muscle, brain, heart, kidney or large intestine), examples of which include tissue damage caused by ischemia, cerebral infarction, stroke, reperfusion injury, myocardial infarction, congestive heart failure, peripheral vascular obstruction, cardiac hypertrophy, low heart contraction, low heart dilatation, maladaptive cardiomegaly, systolic heart failure, diastolic heart failure, hypertensive heart failure, arterial and mitral valve diseases, heart blood vessels with pulmonary valve disease, or regeneration or recovery of ischemic heart blood vessels.

Figure 1:
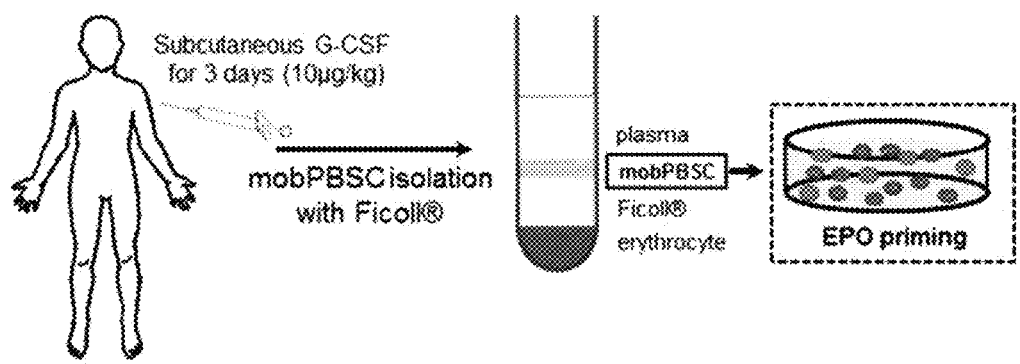
FIG. 1 is a mimetic diagram showing the process of separating mobPBSC—which are mobilized by a cytokine (G-CSF) from human blood based on the difference in densities, and then priming the stem cells in an EPO culture fluid.

In all of the above images, *: $p<0.05$; : $p<0.01$, and *: $p<0.001$.

EMBODIMENTS

In one aspect, the present application relates to a method of producing mobPBSC with improved properties of blood vessel formation, where the method includes providing human-derived peripheral blood that is treated with a cytokine; separating a layer of monocytes from the above blood; and treating the above monocytes with an EPO or an APS.

In the present application, "blood vessel formation" encompasses both "vasculogenesis" and "angiogenesis". Vasculogenesis is characterized by an in-situ differentiation of endothelial progenitor cells into mature endothelial cells and the gathering of such cells to form new blood vessels, as occurs during the formation of a primary vascular plexus in an early embryo. Angiogenesis is caused by the growth of pre-existing blood vessels as well as the growth of blood vessels by branching. In another aspect, it may be derived from pre-existing blood vessels or generated from stem cells, angioblasts or other progenitor cells. The method of measuring the blood vessel formation is well known in the art; for example, it can be determined by measuring the number of unramified vascular segments (the number of segments per unit area segment), density of functional blood vessels (total length of perfused blood vessels per unit area), blood vessel diameter, or bulk density of blood vessels (total volume of blood vessels that is calculated based on the diameter and length of each segment per unit area).

In the present application, cytokine-mobilized PBSC (mobilized Peripheral Blood Stem Cell, mobPBSC) refer to myeloid-derived adult stem cells in blood when peripheral blood is drawn after a treatment with a hemopoietic agent. They can be obtained by the method described in an example of the present application. For example, when a hemopoietic agent such as G-CSF (granulocyte-colony stimulating factor) is injected into a human subject, stem cells in bone marrow are mobilized in the blood circulation system such that a large amount of myeloid-derived adult stem cells can circulate in the whole body. In this case, blood that is richer in myeloid-derived adult stem cells than under normal circumstances can be obtained when drawn from a peripheral area of the body and such cells are named "cytokine mobilized PBSC".

In the present application, an EPO (erythropoietin) increases the hemoglobin level by facilitating the formation of red blood cells and is used as a drug for the treatment of anemia and commercially available, for example, through companies such as LG Life Sciences Ltd. Examples of its use include the treatment of anemia that is observed in patients with chronic renal insufficiency, symptomatic anemia, or the like. It is also known to have a protective effect on nerve cells and cardiac muscle cells.

In the present application, an APS (activated platelet supernatant) is used as the priming material of the present application and can be obtained from blood (e.g. a platelet-rich plasma) that has activated platelets, for example, by the method described in an example of the present application.

In another aspect, the present application also relates to mobPBSC with improved properties of blood vessel formation.

The EPO- or APS-activated cell that is produced according to the present application has the characteristics as follows and can be obtained easily by those skilled in the art by referencing the description or the like in the examples of the present application. Specifically, a cell that is treated with an EPO has, as compared to untreated cells, increased dual expression of integrin beta-1 and -2 and of CD14/CD16, and increased expression of IL8, IL10 and FGF genes and proteins that migrated through an EPO receptor. A cell that is treated with an APS has, as compared to untreated cells, increased gene expression of IL9, IL17, PDGF and VEGF, increased expression of an EPO receptor, CD34, CD31, Tie2, CXCR4, integrin alpha-5, integrin beta-1 and integrin beta-2, and increased dual expression of CD14/CD16.

In another aspect, the present application provides a blood vessel formation accelerator, or a composition for the treatment of a disease that requires properties of blood vessel formation, which contains the cells that are produced according to the method of the present application.

In one embodiment of the present application, an ischemia symptom corresponds to the disease that requires properties of blood vessel formation, and "an ischemia symptom" refers to the state in which the blood supply to tissues is interrupted as the result of bleeding, an embolism, infarction or the like to cause cell damage, and it encompasses various symptoms caused by oxygen deficiency due to an insufficient blood circulation. In the present application, "an ischemic disease" refers to damage in an organ or tissues that are caused by ischemia, or a disease caused by such damage, and it can occur in any of various organs such as a brain, heart, kidney and large intestine, and muscle tissues. For example, brain ischemia may develop into a disease such as stroke and reperfusion injury; in the case of an intestine, ischemic colitis may occur when the blood flow to the large intestine decreases; and cardiac ischemia may develop into myocardial infarction or congestive heart failure.

In one embodiment of the present application, the ischemic disease is an ischemic heart disease and includes cardiovascular tissue damage caused by ischemia. An ischemic heart disease is a cardiac disease caused by decreased blood flow to the heart muscle due to atherosclerosis of a coronary artery or the like, and in a clinical sense, it may be exemplified by, but not limited to, muscle infarction, angina, congestive heart failure, peripheral vascular obstruction, cardiac hypertrophy, low heart contraction, low heart dilatation, maladaptive cardiomegaly, systolic heart failure, diastolic heart failure, hypertensive heart failure, arterial and mitral valve disease, pulmonary valve disease or the like. The composition of the present application that contains APS-primed mobPBSC may be used to facilitate the blood vessel formation of cardiac tissues or to improve cardiac function.

In another embodiment of the present application, the ischemic disease is an ischemic brain disease and includes a disease such as stroke, reperfusion injury and limb ischemia, although it is not limited thereto. The composition of the present application that contains APS-primed mobPBSC may be used in the facilitation of blood vessel formation in brain tissues or in the improvement of brain functions.

In the present application, 'a cell therapy product' refers to a drug that is used for therapeutic, diagnostic and preventive purposes through a series of processes (e.g. the in-vitro proliferation or selection of living autologous, allogenic or xenogenic cells, or the modification of biological properties of cells in other methods) intended to restore the function of cells and tissues. The United States (since 1993) and Korea (since 2002) have managed cell therapy products under the category of medical substances. Such cell therapy products are "stem cell therapy products" for regeneration of tissues or recovery of organ functions and can be categorized as "immune cell therapy products" for controlling immune responses, in other words, for the inhibition or stimulation of in-vivo immune responses.

In the present application, "treatment (therapy)" is a concept that encompasses the inhibition, removal, alleviation, relief, improvement and/or prevention of a disease or a symptom or condition that is caused by a disease.

In the present application, "a therapeutically effective amount" refers to the amount required for the alleviation or treatment of the symptom, condition or disease of a patient. The effective amount of APS-primed mobPBSC, which are contained in the composition of the present application, may vary depending on the route of administration or the age, body weight, underlying disease, normal state of health or the like of the patient, and it will be ultimately determined by the judgement of a physician.

The cells used in the therapeutic composition of the present application are autologous, allogenic or xenogenic cells, and they are particularly autologous cells.

The cell therapy product of the present application may be produced by the method of the present application.

The EPO- or APS-activated mobPBSC of the present application may be analyzed by flow cytometry. Flow cytometry can identify specific markers of the cells of the present application.

Any common route may be used as the route of administration of a pharmaceutical composition containing the cell therapy products or cells of the present application, as long as the medicine can reach the target tissue. Parenteral administration, such as intraperitoneal administration, intravenous administration, intramuscular administration, subcutaneous administration and intradermal administration, may be used, although it is not limited thereto.

The therapy product or composition of the present application can be formulated in a suitable form to be used with a general-use pharmaceutically acceptable carrier(s). A 'pharmaceutically acceptable' composition refers to a composition that is physiologically acceptable and does not typically cause an allergic reaction such as gastrointestinal disorder and dizziness or other similar reactions when administered to a human. Examples of a pharmaceutically acceptable carrier include water, a suitable oil, saline, and a carrier for parenteral administration such as aqueous glucose and glycol, and the carrier may additionally include a stabilizer and a preservative. Examples of a suitable stabilizer include antioxidants such as sodium bisulfite, sodium sulfite, and ascorbic acid. Examples of a suitable preservative include benzalkonium chloride, methyl- or propylparaben, and chlorobutanol. In addition, the composition for cell therapy according to the present invention may suitably contain, if necessary, a suspending agent, a solubilizing agent, a stabilizer, an isotonic agent, a preservative, an adsorption preventing agent, a surfactant, a diluent, an excipient, a pH adjuster, a soothing agent, a buffering agent, an antioxidant or the like, depending on the administration method or formulation. The pharmaceutically acceptable carrier and formulation, including those described above, that are suitable for the present invention are described in detail in the literature [Remington's Pharmaceutical Sciences, latest edition].

The composition for cell therapy according to the present invention may be prepared in a unit-dose form or inside a multi-dose container through formulation using a pharmaceutically acceptable carrier and/or excipient, according to a method that can be easily implemented by those of ordinary skill in the technical field to which the present invention belongs. In this case, the formulation may be in the form of an oil, a solution in an aqueous medium, a suspension or an emulsion, or it may be in the form of a powder, granule, tablet, or capsule.

Also, the above composition may be administered by any device through which a cell therapy product can be moved to a target cell. The composition for cell therapy according to the present invention may contain a therapeutically effective amount of a cell therapy product(s) for the treatment of a disease. The term 'therapeutically effective amount' refers to the amount of an active ingredient or pharmaceutical compound that induces a biological or medical response in a tissue system, animal or human of interest to researchers, veterinarians, medical doctors, or other clinical professionals, and it accounts for the amount that induces the relief of a symptom of the disease or disorder to be treated. It is obvious to those skilled in the art that the cell therapy product to be included in the composition of the present invention may vary depending on the desired effect. Therefore, the optimum cell therapy product content can be readily determined by those skilled in the art and controlled depending on various factors including the type of disease, severity of the disease, amount of other component(s) contained in the composition, type of formulation; age, body weight, normal state of health, sex and diet of the patient; time of administration, route of administration, rate of release of the composition, duration of treatment, and drug(s) that are administered simultaneously. Considering all the above factors, it is important to use the least amount possible with which the maximum effect can be achieved without a side effect. For example, the dosage of the composition of the present invention may be $1.0 \times 10^7$ to $1.0 \times 10^8$ cells/kg (body weight), and preferably $1.0 \times 10^5$ to $1.0 \times 10^8$ cells/kg (body weight) based on the primed mobPBSC. However, the prescribed dosage may vary depending on factors such as the formulation method, mode of administration, the patient's age, weight, sex, pathological conditions, diet, time of administration, route of administration, rate of excretion and reaction sensitivity; the dosage can be controlled suitably by those skilled in the art in consideration of the above factors. Administration frequency may be once, or twice or more within the range of clinically acceptable side effects, and the site of administration may be one, two or more sites. For animals other than humans, a dosage that is the same as that of per kg in a human, or a dosage that is determined by, for example, conversion based on the volume ratio (e.g. average value) of ischemic organs (e.g. heart) of the target animal and a human, may be administered. As the target animal for therapy according to the present invention, a human and a mammal of interest may be exemplified: to be specific, it may be a human, a monkey, a mouse, a rat, a rabbit, sheep, a cow, a dog, a horse, a pig or the like.

Further, the composition of the present application may be used either alone or in combination with a method(s) that use(s) surgery, hormone therapy, drug therapy or a biological response modifier, for the treatment of a disease related to ischemia.

In another aspect, the present application also relates to a method of treating an ischemic disease, where the method includes administering, to a subject who requires the treatment of the ischemic disease, the cells that are prepared according to the present application and a composition that contains the cells. Subjects for whom the treatment method of the present application can be used include mammals, especially humans that require the treatment or prevention of an ischemic disease, and a therapeutically effective amount is administered, where the dosage, cell therapy products and compositions are as described above.

The ischemic disease, for which the treatment method of the present application can be used, are as described above.

Hereinafter, the present invention will be described in more detail with reference to the following examples, but the scope of the present invention is not limited thereto.

Hereinafter, the present invention will be described in more detail with reference to the following examples. However, the following examples are merely provided to facilitate understanding of the present invention, and the invention is not limited by the following examples.

Example 1. Comparison of Cell Properties after Priming of G-CSF-Mobilized PBSC with EPO FIG. 1 schematically illustrates a method for priming mobPBSC, which is mobilized by G-CSF, with an EPO. Four healthy volunteers were recruited after having them sign the consent form, following the approval of the Medical Research Ethics Committee of the Seoul National University Hospital. Peripheral blood had been obtained after receiving the consent in accordance with the Helsinki Declaration. To be specific, G-CSF (Dong-A Pharmaceutical, Korea) was injected once a day at 10 μg/kg into the above volunteers for total of 3 days, and then 100 ml of peripheral blood was obtained using a 50-ml syringe that was treated with heparin. The peripheral blood was divided into 10-ml aliquots, each of which was put in each of 50-ml tubes, then 30 ml of phosphate-buffered saline (PBS) was added and mixed carefully and thoroughly, then 10 ml of Ficoll was added, and then centrifugation was conducted for 30 minutes under the conditions of 2,500 rpm and 25° C. Among the yellow serum layer, white monocyte layer and transparent Ficoll layer at the top and a red layer of red blood cells and polymorphonuclear leukocytes at the bottom, only the white monocyte layer was separated and transferred to a new tube. PBS was added to the transferred monocyte layer, centrifugation was carried out at 1800 rpm and 4° C. for 10 minutes, only the cell pellets were left behind, and then a rinsing process was carried out to obtain a group of high-purity mobPBSC. The mobPBSC obtained as such were put in a culture fluid that was prepared by adding 5% FBS to endothelial basal medium-2 (EBM-2), and an EBM-2 culture medium, which contains an EPO (LG Life Sciences Ltd., Korea) at a final concentration of 10 μM, was used as the priming material. Priming was conducted at a high density of $3 \times 10^7$ cells/ml or more for 6 hours while stirring. The priming condition of 37° C. was maintained in an incubator to which 5% $CO_2$ was supplied.

Figure 2:
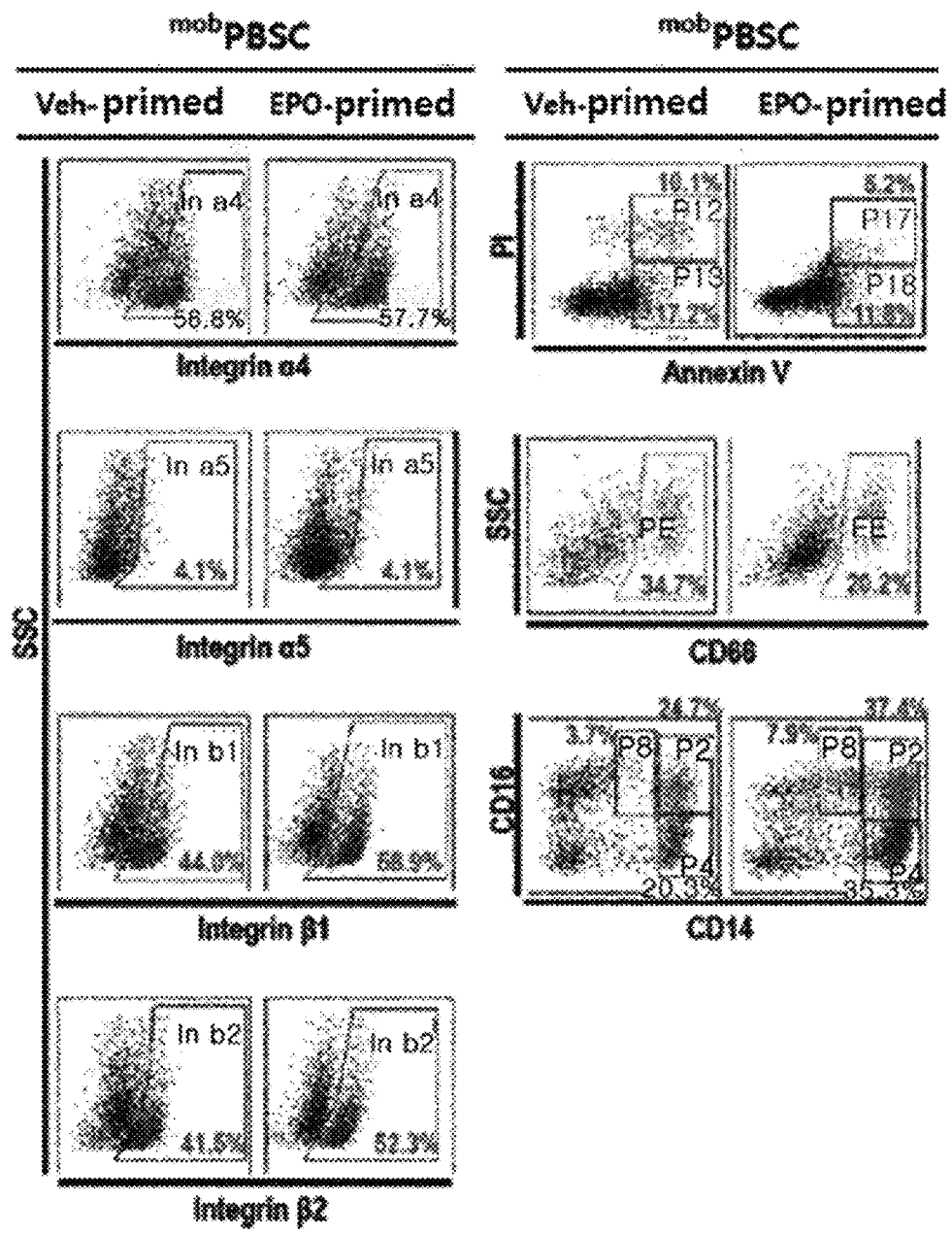
FIG. 2 shows the identified characteristics of cytokine-induced mobPBSC that are primed with EPO through a FACS method.

FIG. 2 shows the results of comparing the properties of G-CSF-mobilized PBSC that were primed with an EPO for 6 hours by a FACS method. The control group and the EPO-primed, G-CSF-mobilized PBSC were stained under the conditions of 30 minutes and 4° C. by using antibodies such as CD14, CD16, CD66, integrin alpha-4, integrin alpha-5, integrin beta-1, integrin beta-2, annexin V and PI, and then the expression was observed by using a FACS device (BD FACS Canto). It was identified from the results that, when priming with an EPO was conducted, the cells in the group that is both CD14- and, CD16-positive increased by about 10% compared to the control group, and that the amount of expression of integrin beta-1 also increased. In addition, it was identified that the cell group that is both positive to annexin V and PI and the cell group that is positive only to annexin V decreased, showing diminished cell necrosis and cell death, respectively.

Example 2. Identification of Angiogenesis-Related Gene and Secretory Protein Expression (In Vitro Test)

Figure 3A:
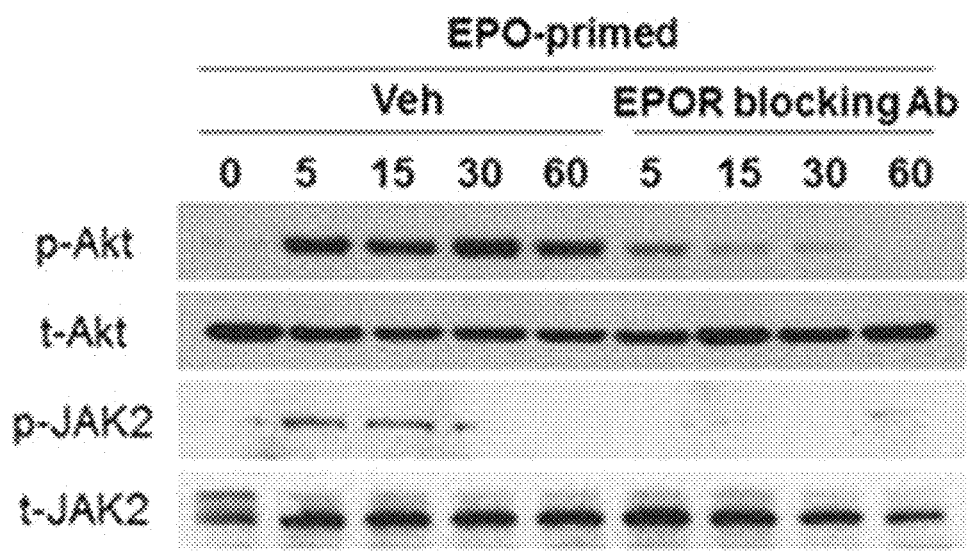
FIGS. 3a and 3b show that the increases in the expression of angiogenesis-related genes and proteins are identified in the cell groups of mobPBSC (mobilized by G-CSF and primed in an EPO culture fluid). Also identified is that such an increase in the expression occurs as downstream JAK, AKT signal transducing molecules are activated as the result of migration through an EPO receptor.

FIG. 3A shows the results of identifying, by western blot, the phosphorylational forms of AKT and JAK signal transducing molecules following the separation of protein(s) at 0 minutes, 5 minutes, 15 minutes, 30 minutes and 60 minutes after EPO-priming of cytokine-mobilized mobPBSC. When stimulated with an EPO, AKT and JAK were activated in 5 minutes, which was inhibited when an EPO receptor was blocked. This indicates that the angiogenesis reaction by an EPO is due to the activation of AKT and JAT signal transducing molecules that migrated through an EPO receptor.

Figure 3B:
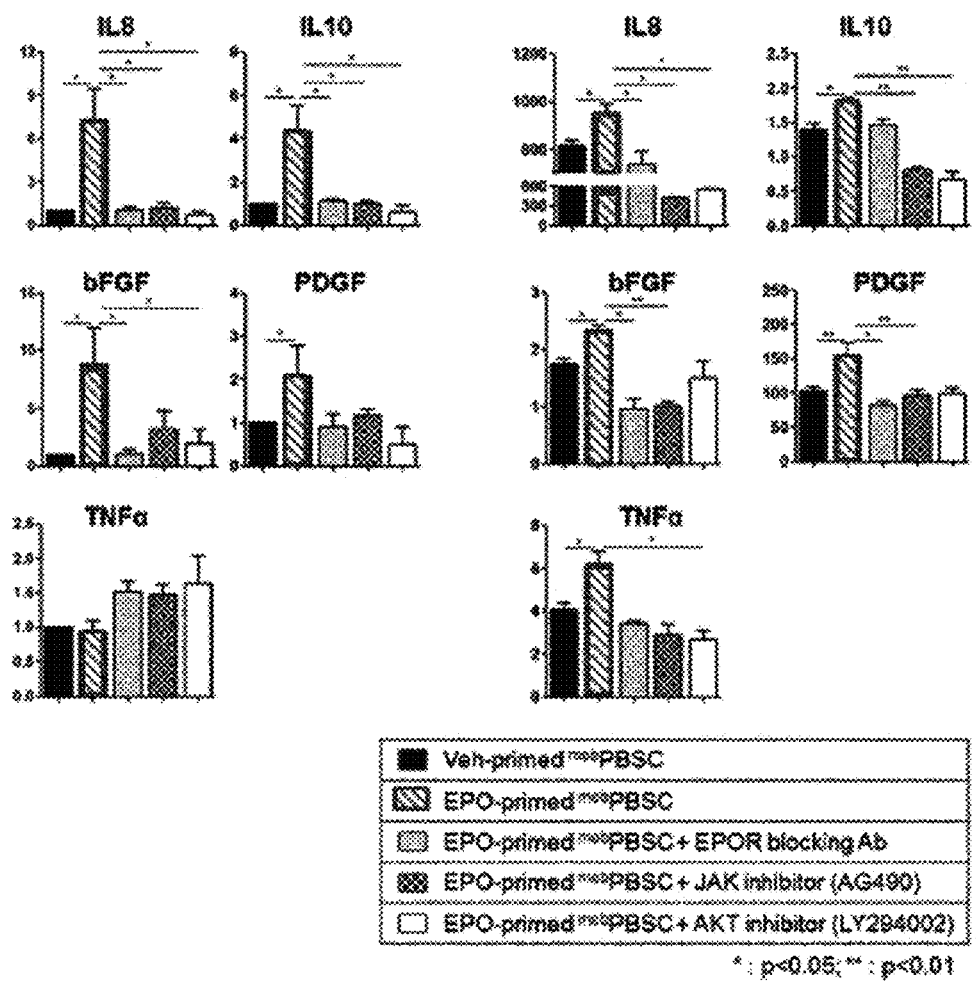

In the left-hand panel graph of FIG. 3B, a reverse transcription-polymerase chain reaction (RT-PCR) was conducted following the separation of total RNA after EPO-priming (under the conditions of 6 hours, 37° C., 5% $CO_2$) of cytokine-mobilized PBSC. Each of the primers used in this case is as in the following Table 1, and the PCR conditions were as follows: 95° C. for 15 seconds, 95° C. for 15 seconds, 60° C. for 1 minute. The results show that the group of EPO-primed mobPBSC had higher gene expression of IL-8, IL-10, bFGF, MMP9, integrin alpha-V and integrin beta-8, which facilitate angiogenesis, compared to the control group.

TABLE 1

| Primer | Sequence | TM | Product size (bp) |
|---|---|---|---|
| IL-8 | FW 5'-GTGCAGTTTTG CCAAGGAGT-3' RV 5'-AATTTCTGTGT TGGCGCAGT-3' | 60 | 135 |
| IL-10 | FW 5'-GCCTAACATGC TTCGAGATC-3' RV 5'-TGATGTCTGGG TCTTGGTTC-3' | 60 | 206 |
| bFGF | FW 5'-GGCTATGAAGG AAGATGGAAGATT-3' TGCCACATACCAACTGG TGTATTT-3' | 60 | 130 |
| MMP9 | FW 5'-GGGCTTAGATC ATTCCTCAGTG-3' RV 5'-GCCATTCACGT CGTCCTTAT-3' | 60 | 94 |

TABLE 1-continued

| Primer | Sequence | TM | Product size (bp) |
|---|---|---|---|
| Integrin alphaV | FW 5'-AATCTTCCAAT TGAGGATATCAC-3' RV 5'-AAAACAGCCAG TAGCAACAAT-3' | 60 | 140 |
| Integrin beta8 | 5'-AATTTGGTAGTGGA AGCCTATC-3' 5'-GTCACGTTTCTGCA TCCTTC-3' | 60 | 146 |

In the right-hand panel graph of FIG. 3B, the expression of a cytokine, which is known to facilitate angiogenesis, in EPO-primed mobPBSC was comparatively analyzed by ELISA. The results identify that the amounts of secretion of IL-8, IL10, TNF-alpha which are known to be a factor related to blood vessel formation are higher with EPO-primed mobPBSC than in the control group. In addition, it was identified that a reaction caused by an EPO decreases when an EPO blocking antibody, a JAK inhibitor and an AKT inhibitor are treated. ELISA was conducted by using a Bio-Plex Prot™ Array System (kits and equipment of Bio-Rad, USA) as used by the manufacturer.

Example 3. Identification of Effectiveness of Vasculogenesis (In Vitro Test)

Figure 4A:
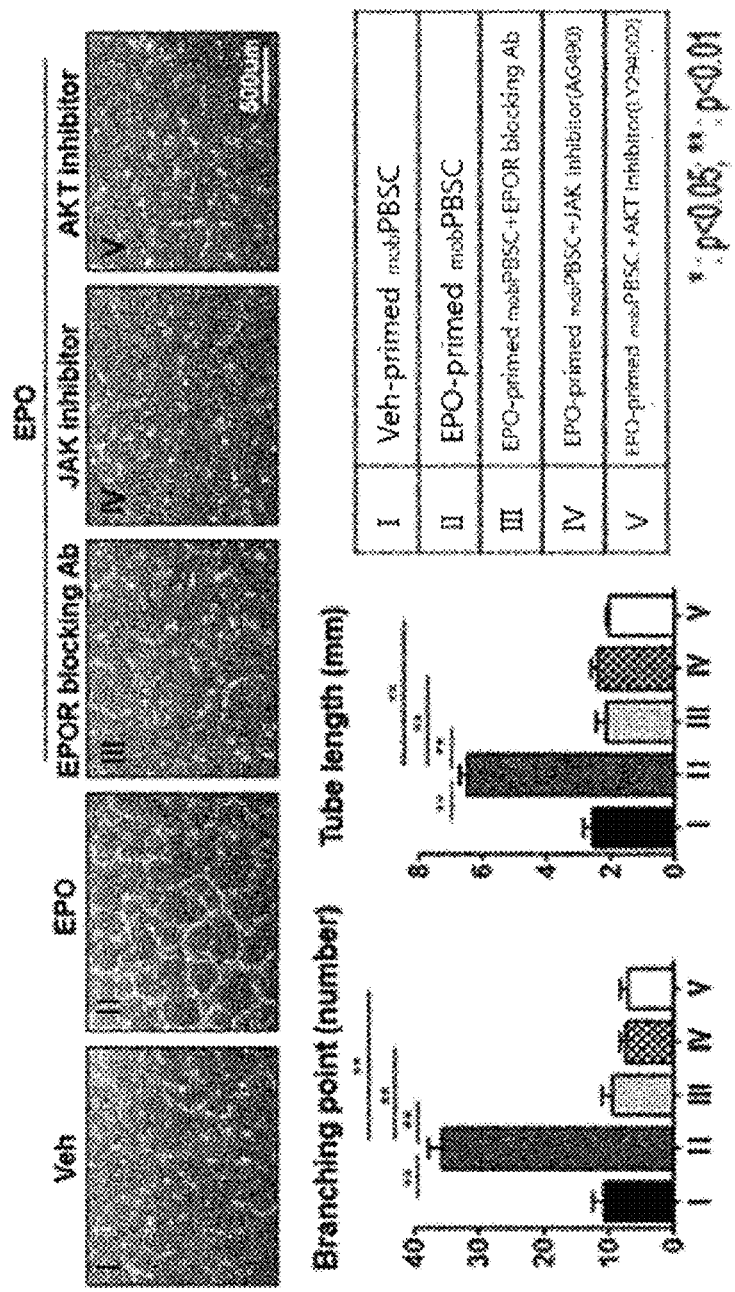
FIGS. 4a and 4b show that the human umbilical vein endothelial cells (HUVEC) ability of tube formation and migration improves when the cell culture supernatant of the cell groups of mobPBSC (mobilized by G-CSF and primed in an EPO culture fluid) is treated and that such an improvement occurs by migration through an EPO receptor.

FIG. 4 shows the results of identifying, by using the supernatant of cytokine-induced mobPBSC that were primed with the EPO-priming formulation of Example 1, differences in vasculogenesis properties and mobility of HUVEC in Matrigel. It was also identified that this was due to the activation of downstream JAK and AKT signal transducing molecules that migrated through an EPO receptor. In FIG. 4A, the bottom of a 35 mm confocal dish (ibidi, Germany) was placed on ice and coated with 200 μl of GFR Matrigel (BD Biosciences) and then incubated at 37° C. for about 30 minutes. Then, HUVEC ($2 \times 10^4$) were carefully placed on the 35 mm confocal dish (previously coated with Matrigel) by having the supernatant of EPO-primed cytokine-induced mobPBSC as the culture fluid. 12 hours later, the tube-forming ability of HUVEC was evaluated under a microscope, and it was identified that the tube-forming ability (the number of branching points and the tube length) of HUVEC was greater with EPO-priming. Also it was identified that an increase in the tube-forming ability deteriorated when treated by each of an EPO receptor-blocking antibody, a JAK inhibitor (AG490) and an AKT inhibitor (LY294002).

Figure 4B:
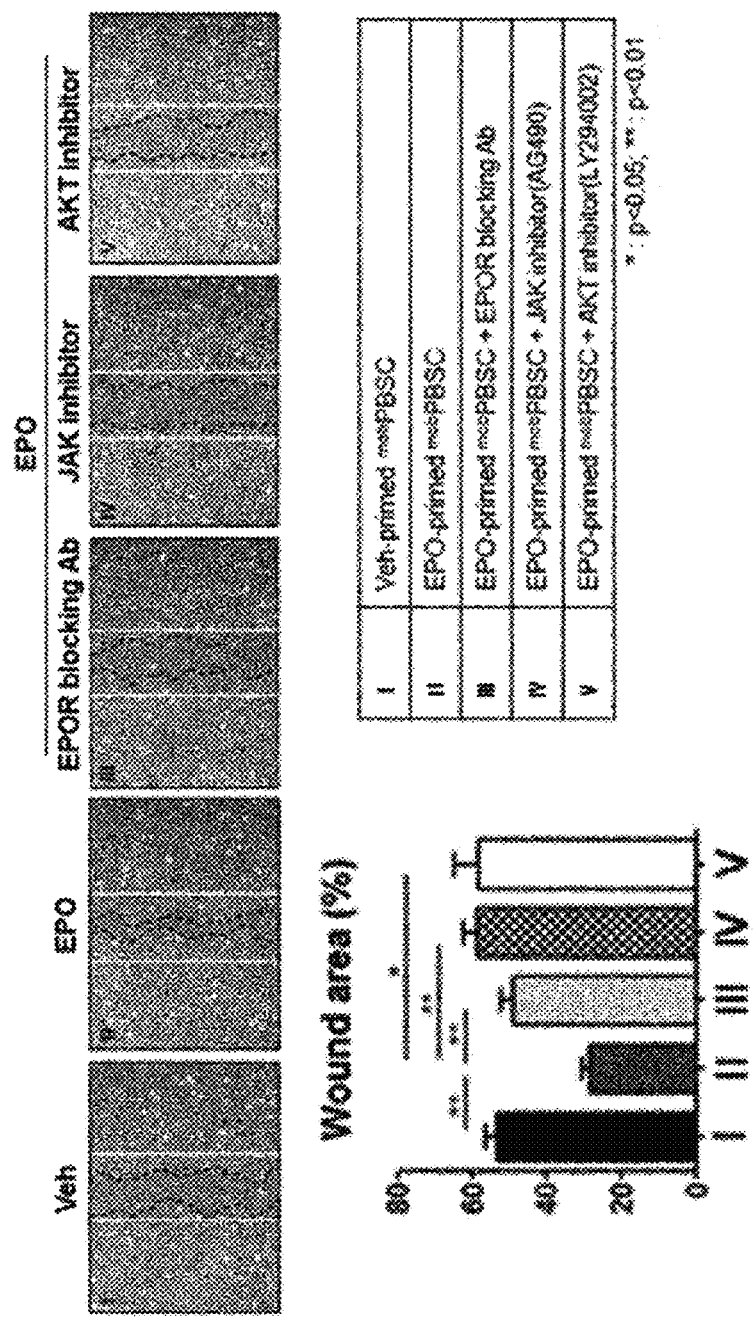

In FIG. 4B, HUVEC were incubated on a dish for one day, a line-shaped scratch with uniform thickness was made, and then the culture fluid of EPO-primed mobPBSC was added to evaluate the HUVEC' ability to migrate. As seen in FIG. 4 B, when the culture fluid with EPO-primed mobPBSC was used, the mobility of HUVEC was greater compared to the control group. Also, it was identified that an increase in the tube-forming ability deteriorated when treated by each of an EPO receptor-blocking antibody, a JAK inhibitor (AG490) and an AKT inhibitor (LY294002). It was confirmed by an in-vitro test that the vasculogenesis properties of vascular endothelial cells of cytokine-mobilized mobPBSC improved as such with EPO-priming.

Figure 5A:
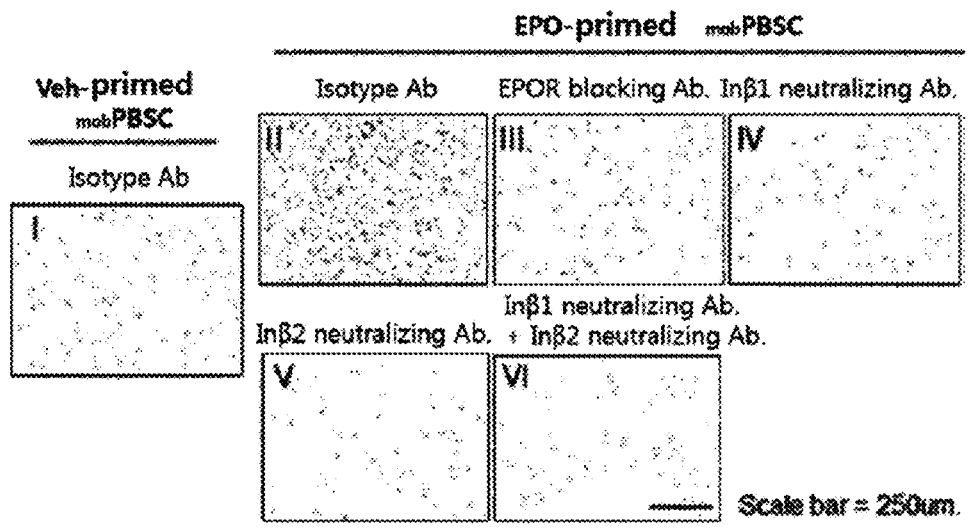
FIGS. 5a-5c show that the cell groups of mobPBSC (mobilized by G-CSF and primed in an EPO culture fluid) exhibit stronger attachment to HUVEC and ECM (fibronectin) and that such a phenomenon is due to increased integrins.
Figure 5B:
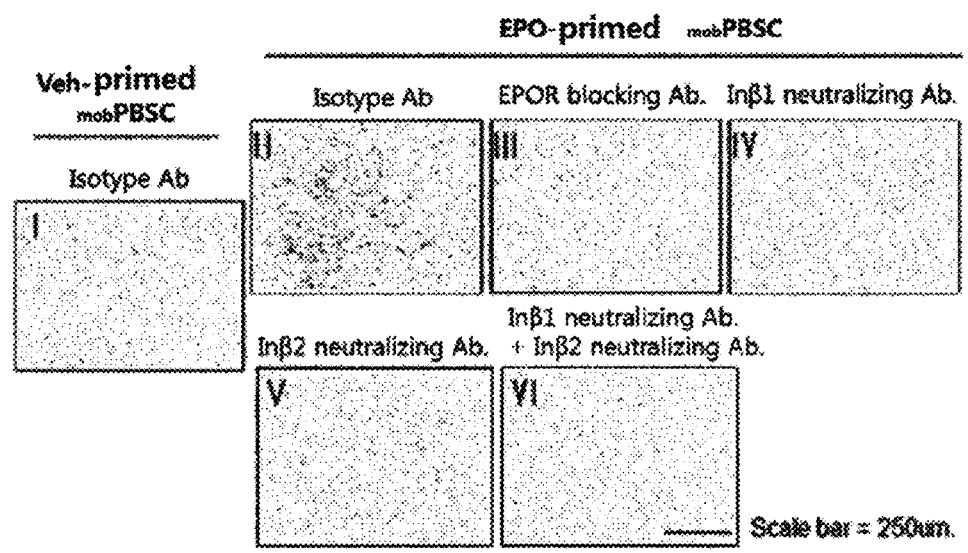
Figure 5C:
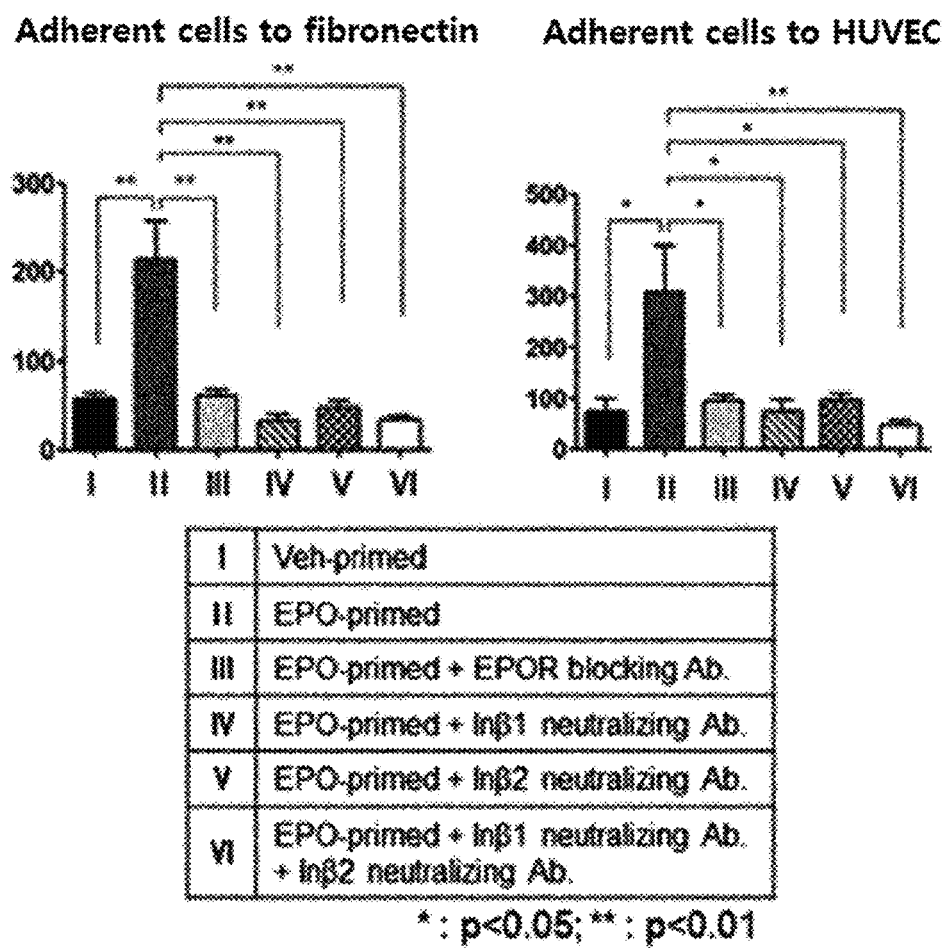

In FIG. 5, the control group and the EPO-primed cytokine-mobilized PBSC was stained with 5-(and -6)-carboxyfluorescein diacetate succinimidyl ester (CFSE; Sigma-Aldrich, USA) at 37° C. for 1 hour, and then $2 \times 10^5$ cells were evaluated on the ability to attach to either one of HUVEC and ECM (fibronectin) for 1 hour. It was identified through the results that the EPO-primed cytokine-mobilized mobPBSC, compared to the control group, had a greater ability to attach to either one of HUVEC and fibronectin and that an increase in the ability to attach deteriorates when an integrin-blocking antibody was used. With these results, it was identified that the ability of cytokine-mobilized mob-PBSC to attach to extracellular matrix and to vascular endothelial cells increased with EPO-priming. Furthermore, it is assumed by such an increase in the ability to attach that the cell engraftment to actual active sites can increase.

Example 4. Determination of Effect of Vasculogenesis (In Vivo Test)

Figure 6A:
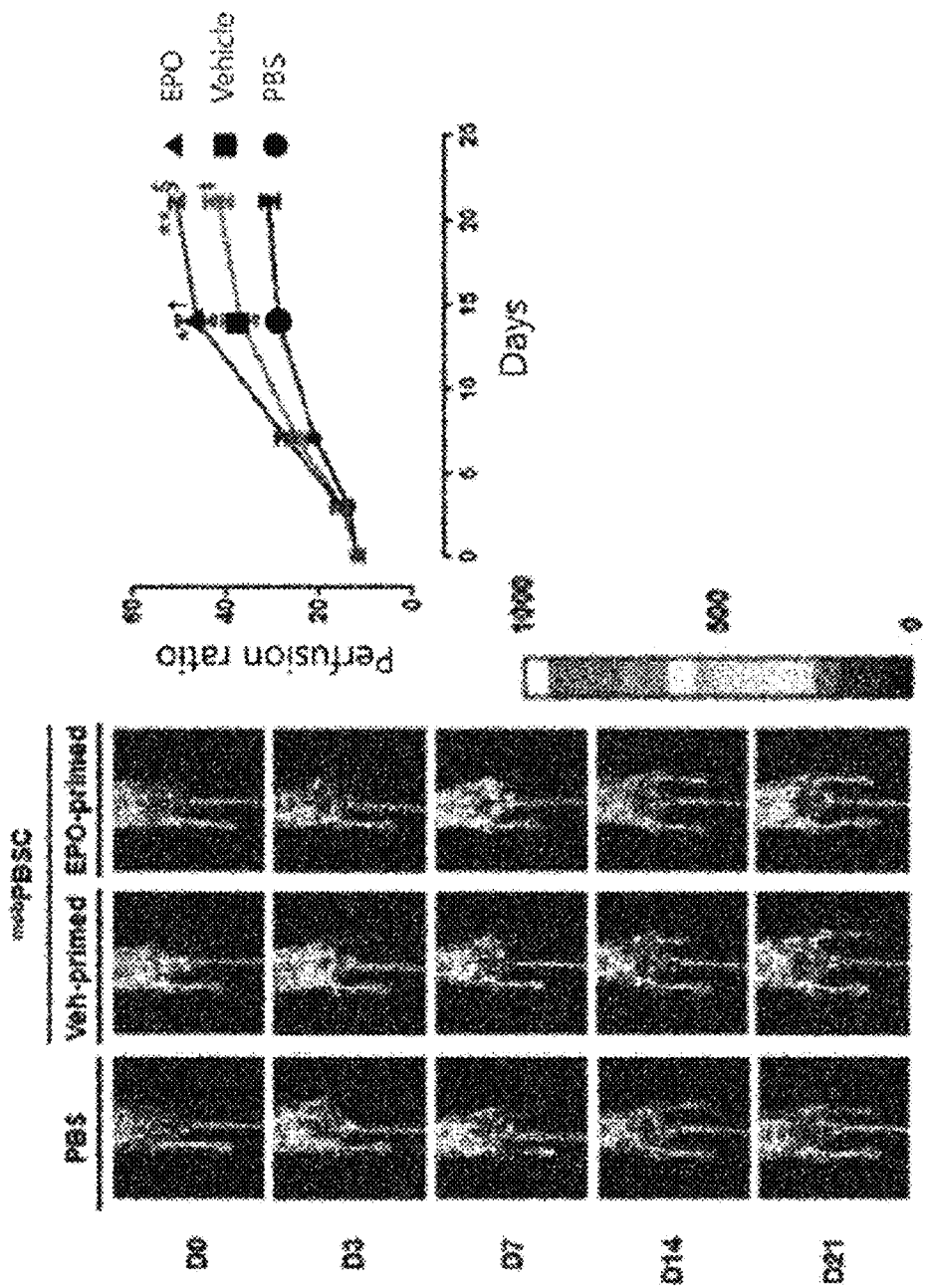
FIGS. 6a-6c show that excellent properties of blood vessel formation are observed, when an ischemic hindlimb model of an athymic nude mouse with an inhibited immune system is prepared and then mobPBSC (mobilized by a cytokine and EPO-primed) are injected into the mouse. Also identified is that, when immunofluorescence staining of hindlimb tissues is carried out 21 days later by using CD34 (cluster of differentiation 34 (green color): an antibody that is specific to human cells), which is a vascular endothelial cell primer, mobPBSC that are mobilized by G-CSF and primed in an EPO culture fluid are incorporated in vasculogenesis.
Figure 6B:
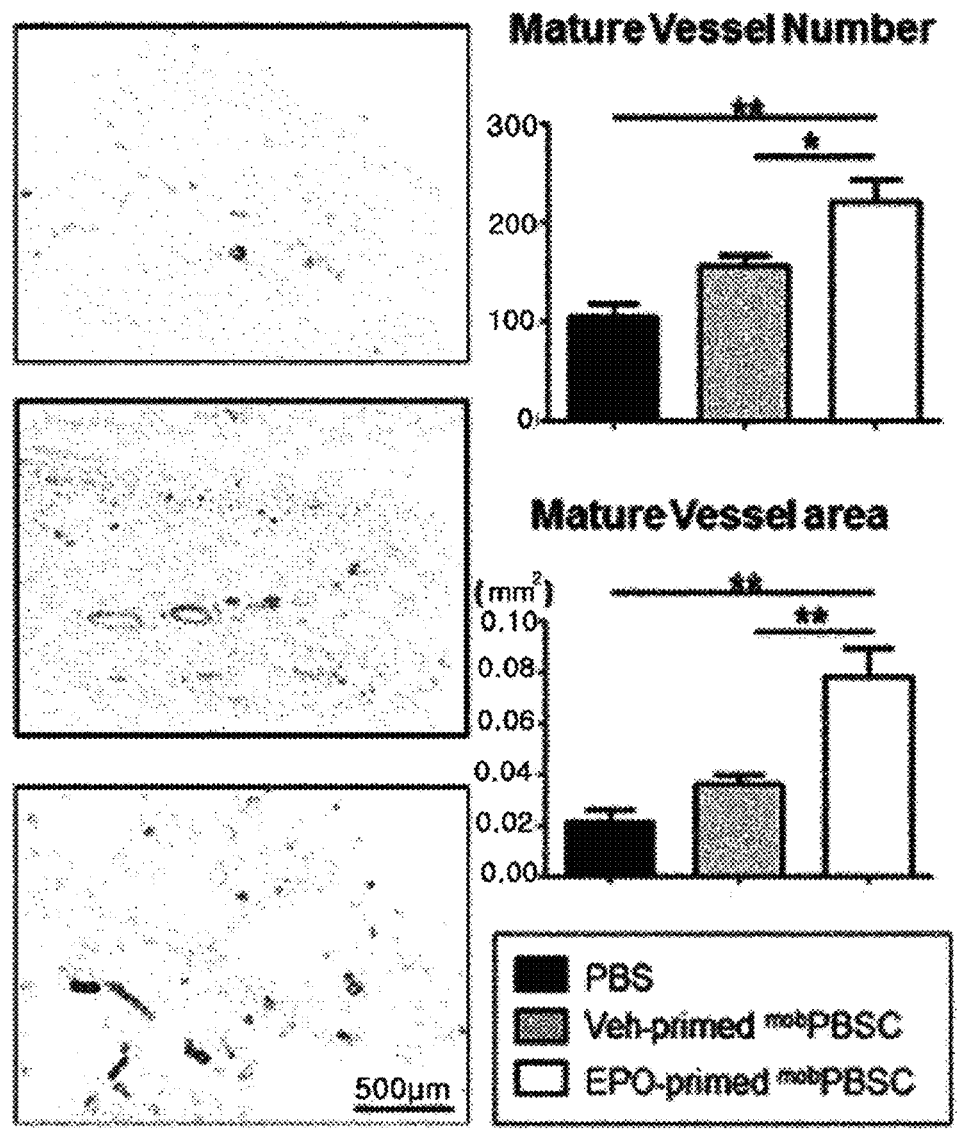

FIG. 6 shows that an increase in vasculogenesis in a pre-clinical stage is greater with EPO-primed cytokine-mobilized PBSC, as compared with the unprimed control group. To be specific, an ischemic condition was induced in the hindlimb of each of athymic nude mice (BAL/c-nu, aged 6-8 week, 16-20 g, Oriental Bio, Korea) with an inhibited immune system, and the injection of one of PBS, unprimed control group ($3 \times 10^5$ cells) and EPO-primed cytokine-mobilized PBSC ($3 \times 10^5$ cells) was performed. Perfusion was measured by LDPI (Laser Doppler perfusion imaging) immediately after the induction of ischemia, and 3, 7, 14, 21 days after the induction of ischemia. The results indicate that, as seen in FIG. 6A, perfusion was greater in the EPO-primed mobPBSC (n=7) as compared with the group into which PBS (n=7) or vehicle-primed mobPBSC (n=7) was/were injected. In addition, the results of staining alpha smooth muscle actin (SMA-α, red color) to observe mature blood vessels indicate that more blood vessels were formed, as seen in FIG. 6B, when EPO-primed mobPBSC were injected. Upon quantification, it was identified from the results that the number of tubes, tube area and tube length significantly increased upon injection of EPO-primed mob-PBSC, as compared with the groups into which PBS or vehicle-primed mobPBSC was/were injected.

Figure 6C:
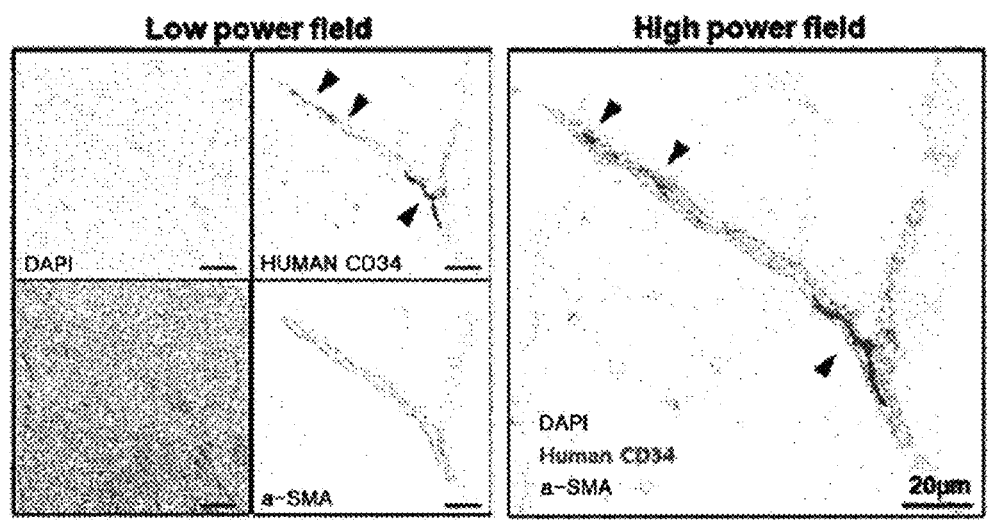

In FIG. 6C, from the results of immunofluorescence staining of CD34 (cluster of differentiation 34, green color), which is a vascular endothelial cell marker, with SMA-α (red color) and antibody specific to human cells, it was identified that the cells into which EPO-primed mobPBSC were injected were actually enabled to undergo vasculogenesis.

Figure 7:
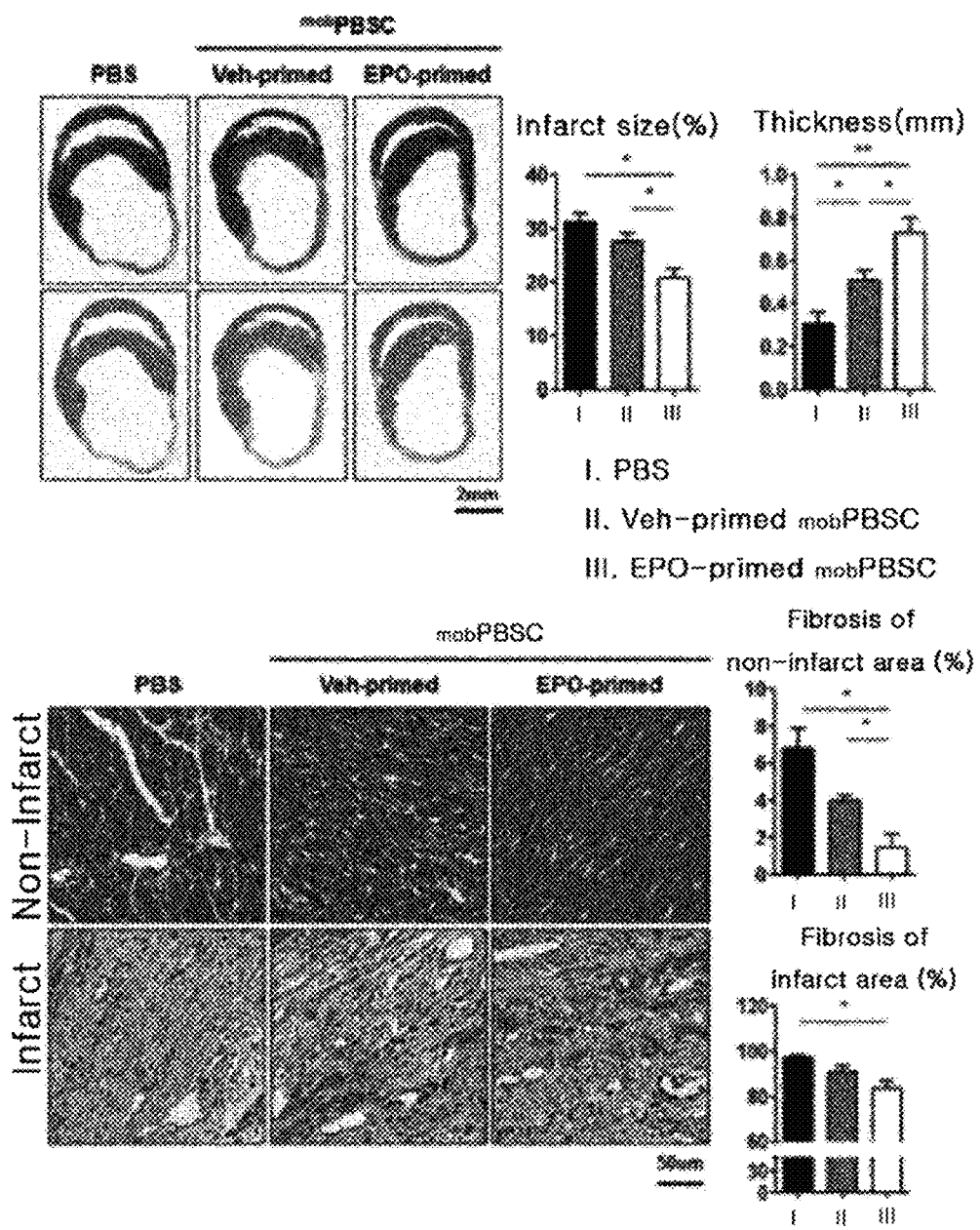
FIG. 7 shows that the recovery of a heart is facilitated when mobPBSC (mobilized by a cytokine and EPO-primed) are injected into an athymic nude mouse with an inhibited immune system, following the induction of ischemia to the heart of the mouse.

In FIG. 7, an ischemic condition was induced in the heart of each of athymic nude mice (BAL/c-nu, aged 6-8 week, 16-20 g, Oriental Bio) with an inhibited immune system, and the injection of one of PBS (n=6), control group of the present invention ($3 \times 10^3$) (n=6) and EPO-primed cytokine-mobilized mobPBSC ($3 \times 10^3$) (n=6) was performed. 14 days later, the heart was taken out, subjected to MT (Masson's trichrome) staining and H&E (Hematoxylin and eosin), and then the size of ischemia, thickness of left heart wall and ratio of fibrosis area were measured. It was identified from the results that the ischemic heart into which EPO-primed cytokine-mobilized mobPBSC were injected recovered the most.

Example 5. Preparation of mobPBSC and APS and Analysis of APS

Four healthy volunteers were recruited after having them sign the consent form, following the approval of the Medical Research Ethics Committee of the Seoul National University Hospital. Peripheral blood had been obtained after receiving the consent in accordance with the Helsinki Declaration.

Figure 8A:
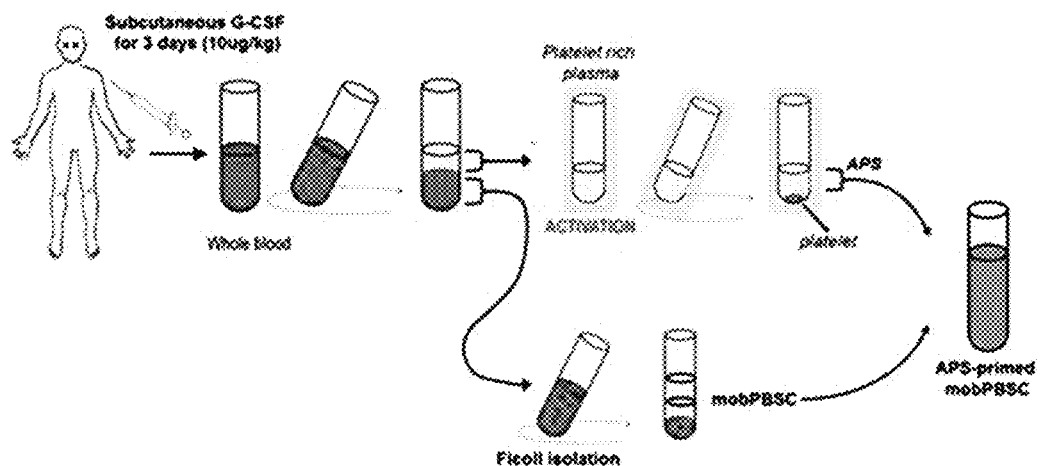
FIGS. 8a-8c show a schematic of the method of priming mobPBSC with APS, the result of Giemsa staining after separation of the mobPBSC, and the result of an analysis with ELISA (enzyme-linked immunosorbent assay) on cytokines with respect to an unactivated platelet supernatant (naive platelet supernatant) and APS.
Figure 8B:
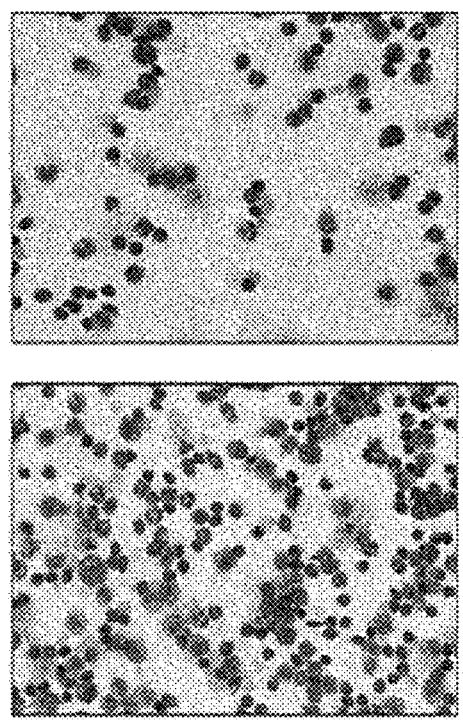

The mobPBSC were obtained as described in Example 1. The obtained cells were subjected to priming, immediately after being obtained, with an APS for 6 hours as described below, and the process is schematically illustrated in FIG. 8A. All separation processes were carried out in a sterile environment, and the purity of separated mobPBSC was evaluated by Giemsa staining (see FIG. 8B).

To obtain an APS, first, 100 ml of peripheral blood that was acquired from each volunteer was subjected to centrifugation at room temperature for 20 minutes at 130×g (700 rpm) to separate PRP (platelet rich plasma). The PRP was transferred to a new test tube, PBS including heparin (at 400 U/ml) was added, and centrifugation was performed at room temperature at 900×g (2000 rpm) for 7 minutes. The supernatant was removed thereafter, and then the above process using PBS containing 400 U/ml of heparin was repeated for two more times. 0.5 U/ml of thrombin (Sigma-Aldrich, USA) was added to 10 ml of final amount of the platelets obtained as the above, and the platelets were activated in an incubator (37° C., 5% $CO_2$) for 2 hours. Upon completion of activation, the platelet was removed by centrifugation at 10000×g at room temperature for 10 minutes, and only the supernatant was collected and used for the 6 hours of priming in an incubator (37° C., 5% $CO_2$). The experimental process is schematically illustrated in FIG. 8A.

Figure 8C:
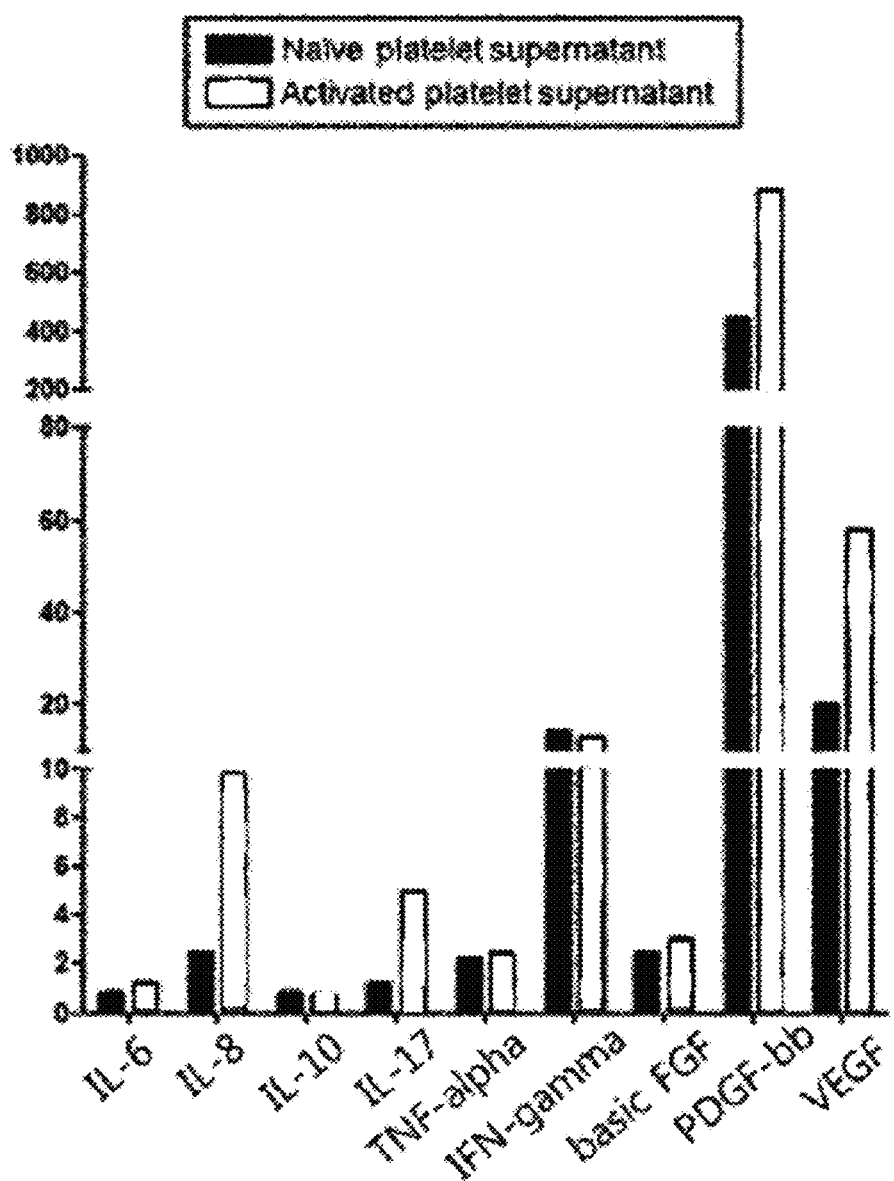

FIG. 8C shows the results of ELISA that was used to analyze a naive platelet supernatant and APS for a secreted cytokine. The results show that the expression of IL-8, IL17, PDGF and VEGF was greater compared with the control group. ELISA was performed by using a Bio-Plex Prot™ Array System (kits and equipment of Bio-Rad, USA).

Example 6. Study of Expression and Function of Angiogenesis-Related Gene and Primer (In Vitro Test)

Figure 9:
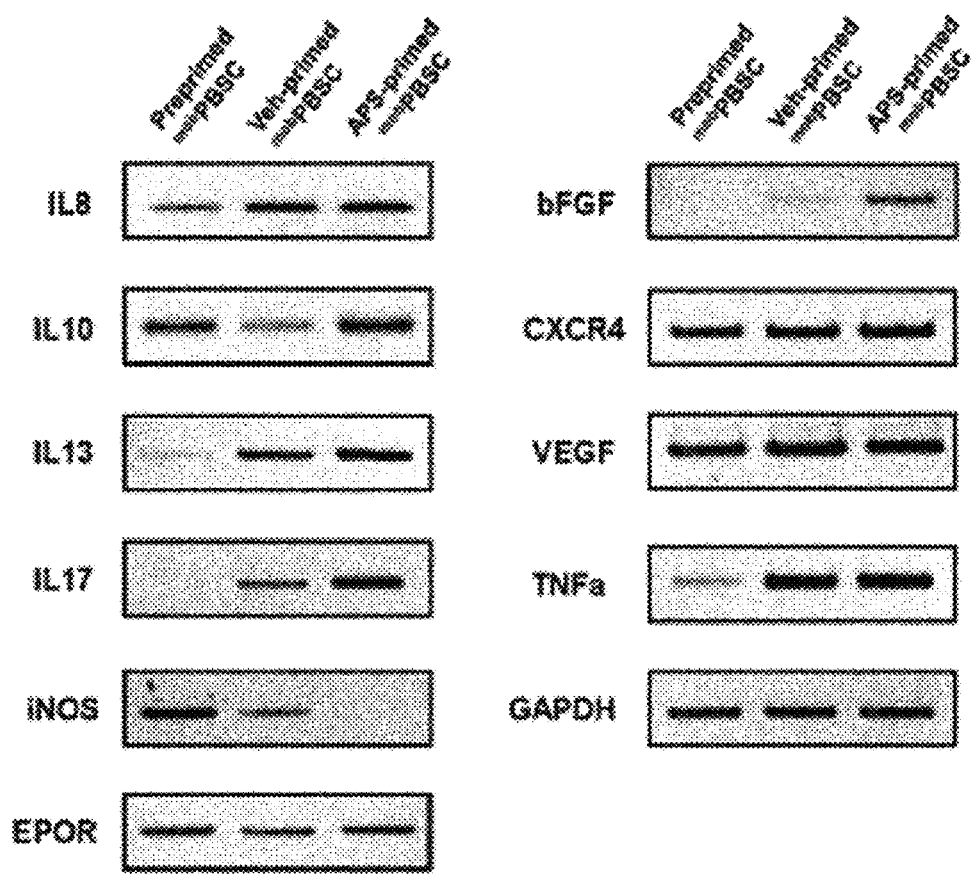
FIG. 9 is an analyzed result of RT-PCR on the gene expression of IL-8, IL-10, IL-13, IL-17, bFGF, TNF-, CXCR4 and EPOR (erythropoietin receptor) after 6 hours of stimulation (with Veh/APS) of mobPBSC.

FIG. 9 shows the results of incubating (37° C., 5% $CO_2$ incubator) mobPBSC with an APS for 6 hours, then separating RNA to conduct RT-PCR. Total RNA was obtained with TRIzol (Invitrogen, USA) Reagent by the method described clearly by the manufacturer. cDNA was synthesized by using a Primescript $1^{st}$ strand cDNA synthesis kit (TAKARA, Japan) according to the method provided by the manufacturer. The amplification process was carried out by using Maxime™PCR (Intron, Korea) with the reaction mixture and the total amount of 20 µl. The primers used are as in Table 2, and the PCR conditions were as follows: 95° C. for 15 seconds, 95° C. for 15 seconds, 60° C. for 1 minute. The results show that expression of IL-8, IL-10, IL-13, IL-17, bFGF, TNF-α, CXCR4 and EPO receptor (EPOR) genes, which facilitate blood vessel formation, was higher in APS-primed mobPBSC as compared with vehicle-primed mobPBSC.

| primer | | Sequence | Tm (° C.) | bp |
|---|---|---|---|---|
| IL8 | FW | GGCCGTGGCTCTCTTGGCAG | 62 | 178 bp |
| | RV | TGTGTTGGCGCAGTGTGGTC | | |
| IL10 | FW | GCCTAACATGCTTCGAGATC | 62 | 206 bp |
| | RV | TGATGTCTGGGTCTTGGTTC | | |
| IL13 | FW | TAGGGAGGGGTAAAATTCCT | 58 | 335 bp |
| | RV | CGGTGACAAACACACTCATT | | |

| primer | | Sequence | Tm (° C.) | bp |
|---|---|---|---|---|
| IL17A | FW | GACCTCATTGGTGTCACTGCTAC | 58 | 326 bp |
| | RV | GGACAGAGTTCATGTGGTAGTCC | | |
| bFGF | FW | TCTTCAACACCGAAATGCTG | 62 | 206 bp |
| | RV | AGCCCAGTTAGAGGGACCAT | | |
| TNFa | FW | CCCTGAAAACAACCCTCAGA | 58 | 217 bp |
| | RV | AAGAGGCTGAGGAACAAGCA | | |
| iNOS | FW | CATCAACAACAATGTGGAGAAAGC | 62 | 378 bp |
| | RV | TGGTTGACAAATTCGATAGCTTGA | | |
| EPOR | FW | GAGATGCCAGAGTCAGATACCAC | 62 | 301 bp |
| | RV | AGGATACCTATCTGGTGCTGGAC | | |
| CXCR4 | FW | AGTCAACCTCTACAGCAGTGTCC | 62 | 388 bp |
| | RV | CAGGATGAGGATGACTGTGGTCT | | |
| GAPDH | FW | GGGTGTGAACCATGAGAAGTATGA | 62 | 368 bp |
| | RV | CATATTTGGCAGGTTTTTCTAGACG | | |

Figure 10:
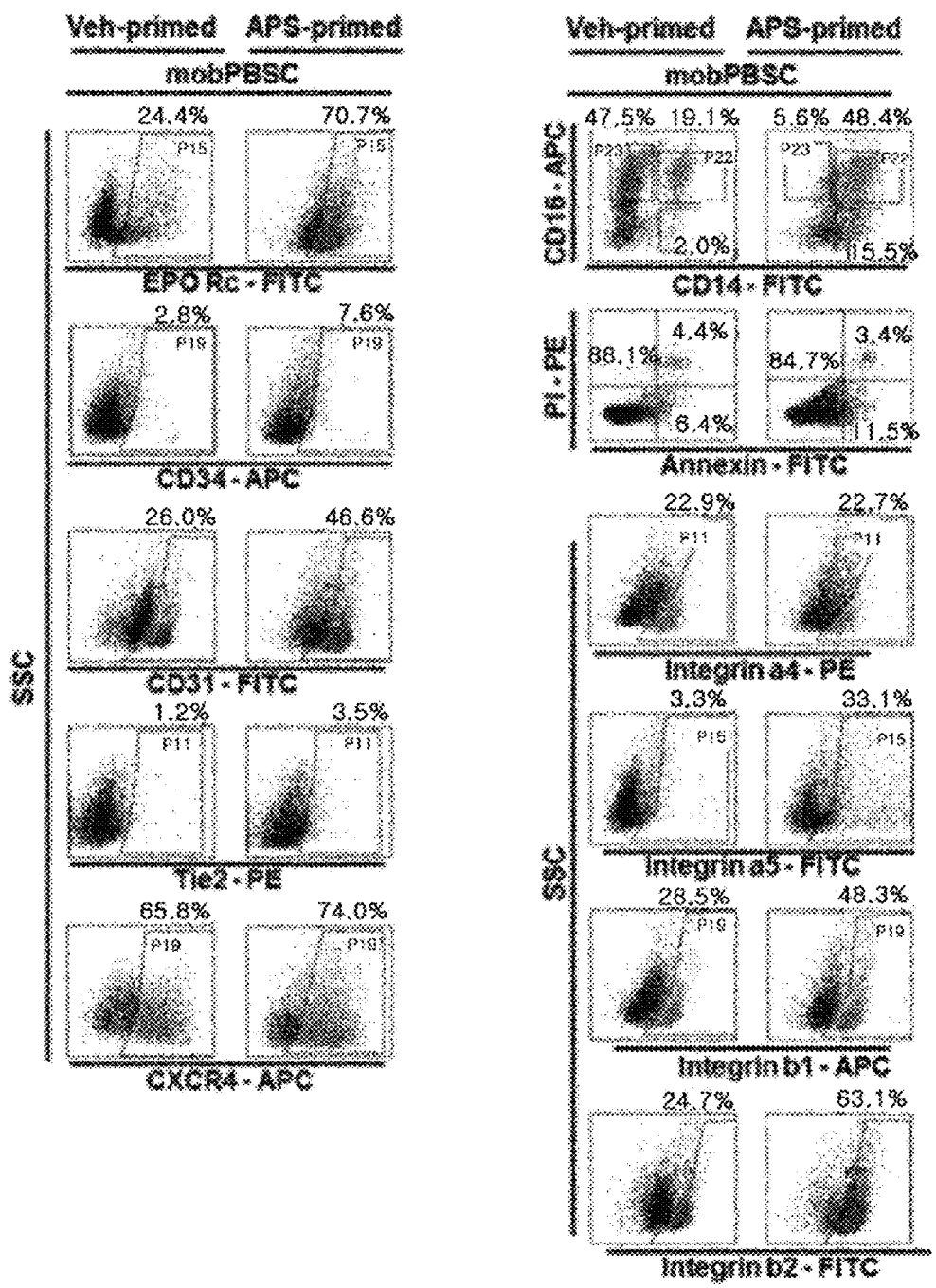
FIG. 10 shows the identified characteristics of mobPBSC that are Veh/APS-primed by a FACS method.

FIG. 10 is the result of analyzing, by using FACS (fluorescence-activated cell analysis) that utilizes fluorescence, various antibodies on the cell surface of APS-primed mobPBSC and of the control group. Together with BD FACS Canto as the FACS, FITC-labeled anti-EPO receptor (R&D, USA), Annexin V (Becton Dickinson), Integrin alpha-5 (eBioscience, USA) and Integrin beta-2 (Becton Dickinson) antibody; APC-labeled anti-CD16 (eBioscience), CD31 (Becton Dickinson), CD34 (Becton Dickinson) and CXCR4 (eBioscience) antibody; PEcy7-labeled anti-CD14 (eBioscience) antibody; PE-conjugated anti-Tie2 (R&D), PI (Becton Dickinson, USA), Integrin alpha-4 (R&D) and Integrin beta-1 (Becton Dickinson) antibody were used, and IgG was used as the control group. Compared to vehicle-primed mobPBSC, APS-primed mobPBSC exhibited a larger increase in EPOR-positive cells, which facilitate angiogenesis. Moreover, CD34-positive cells (which are markers for hematopoietic stem cells), and CD31-, Tie2- and CXCR4-positive cells (all of which are markers for blood vessel formation) also increased. Also, CD14(++)/CD16(+) cells, which are monocytes for blood vessel formation, increased. In contrast, Annexin (+)/PI (+) cells, which are markers for apoptosis, decreased. It was identified that an increase in the number of cells that express integrins α5, β1 and β2, which are important integrins in angiogenesis, was more evident in APS-primed mobPBSC than in vehicle-primed mobPBSC.

Example 7. Identification of Effect of Vasculogenesis (In-Vitro Test)

Figure 11:
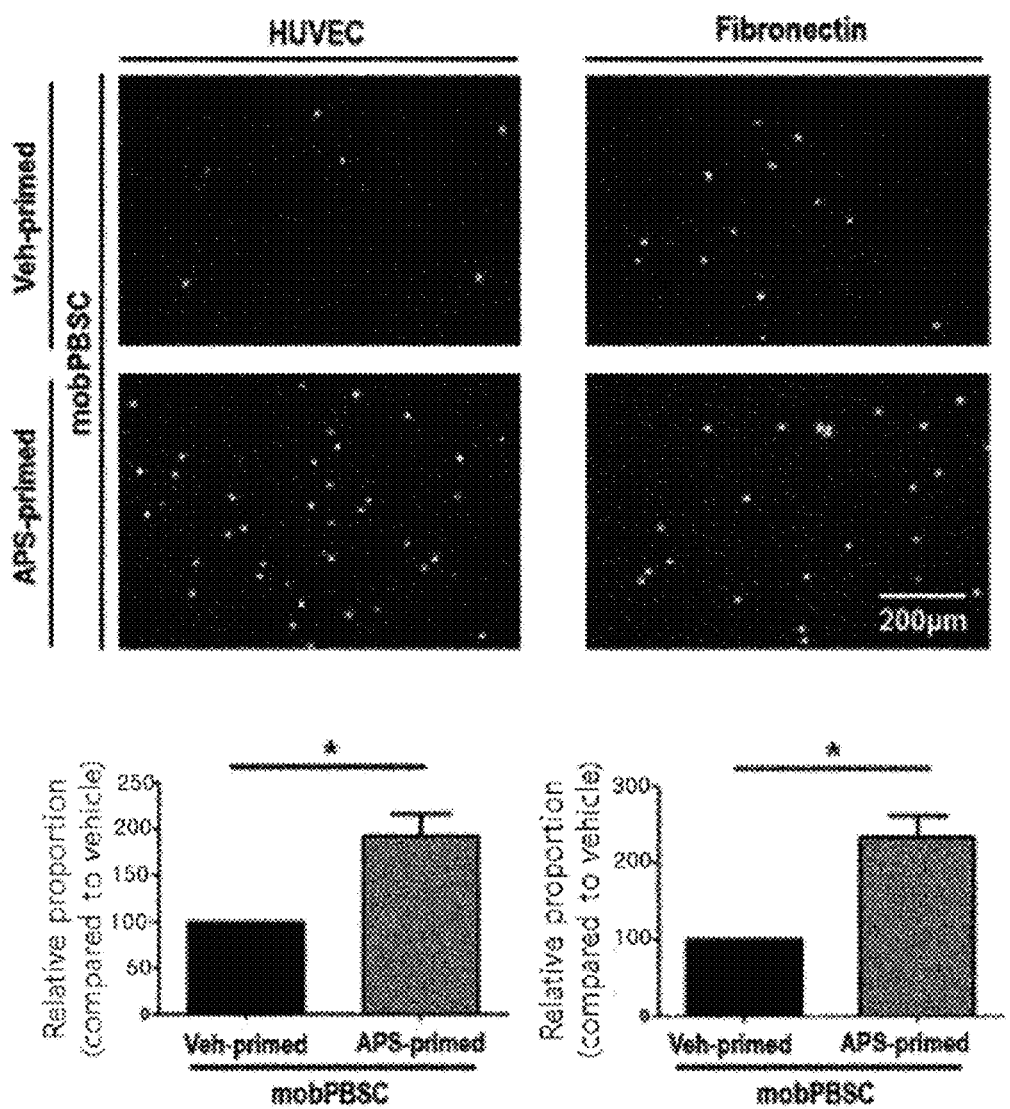
FIG. 11 shows the observed results of a fibronectin attachment in Veh/APS-primed mobPBSC.

In FIG. 11, seeding of HUVEC as a single layer in a fibronectin-coated 24-well plate was performed one day earlier for the examination of primed mobPBSC' ability to attach to either one of HUVEC and ECM (extra-cellular matrix). mobPBSC were stained with CFSE (5-(and -6)-carboxyfloresein diacetate succinimidyl ester, Sigma-Aldrich, USA) in an incubator for an hour (37° C., 5% $CO_2$). mobPBSC ($2 \times 10^5$) stained with CFSE were put in each of the prepared 24-well and then put in an incubator (37° C., 5% $CO_2$) to observe. The results were obtained by rinsing the floating mobPBSC with PBS, then photographing—under a 40x-magnitude microscope, at 10 different spots—only the fluorescence in the mobPBSC (which were still attached), and quantifying the primed-mobPBSC that migrated toward SDF-1a. According to the result, an increase in attachment to HUVEC and fibronectin was more evident in APS-primed mobPBSC than in vehicle-primed mobPBSC.

Figure 12A:
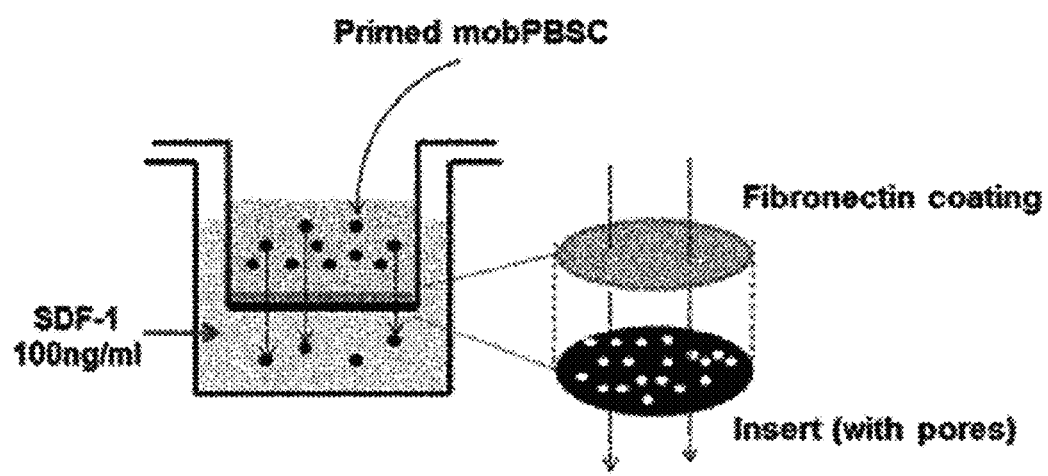
FIGS. 12a and 12b show a schematic of experimental process to identify a chemotaxis and a cell migration, and the observed results of a chemotaxis of Veh/APS-primed mobPBSC toward SDF-1.
Figure 12B:
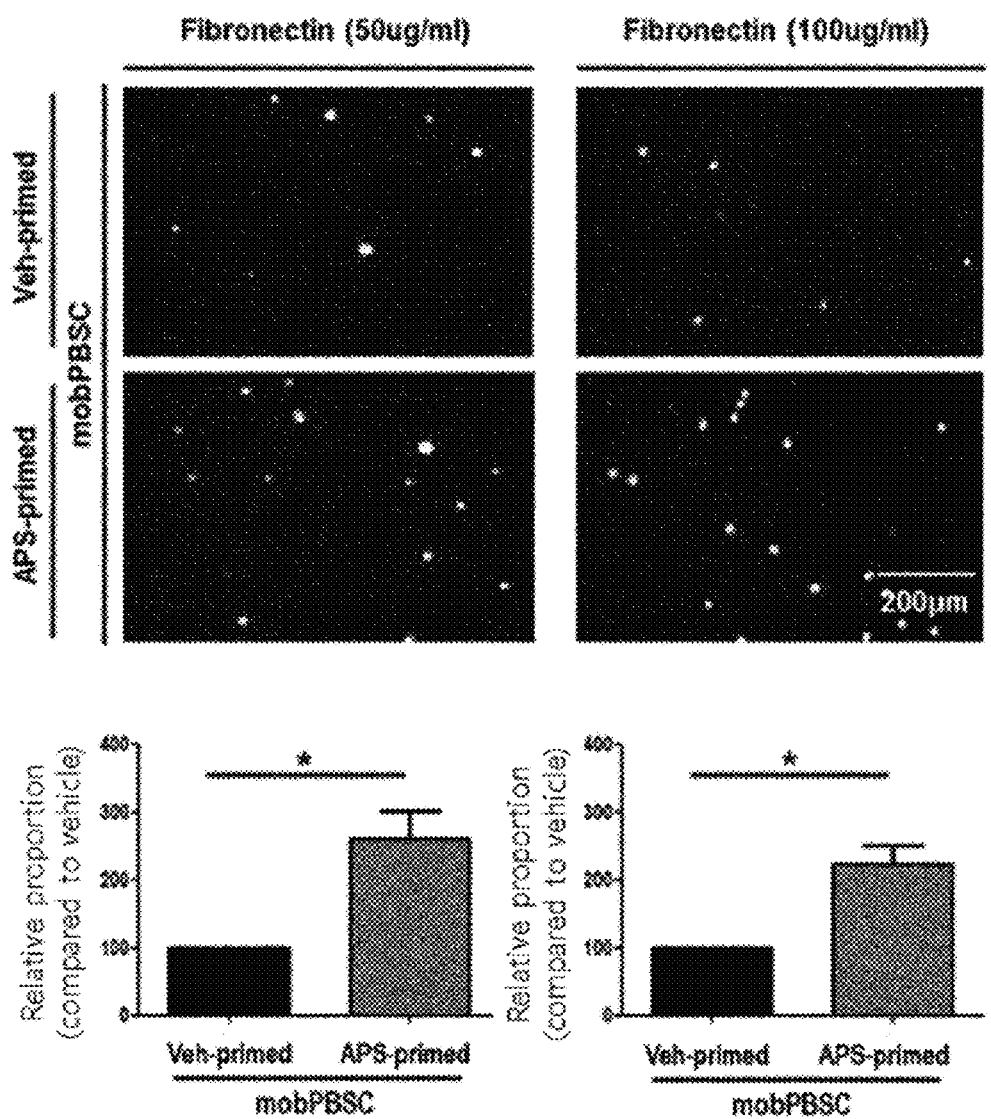

FIG. 12A schematically illustrates the testing process for the observation of chemotaxis and cell migration. To be specific, the analysis of chemotaxis was performed by using a 24-well plate(s) and a transwell filter(s) (5 uM pore size, Corning, USA). The transwell filter was coated with 50 µg of fibronectin at 100 µg/ml. As in the analysis of chemotaxis, mobPBSC were stained with CFSE. For the test, an EBM2 culture medium containing recombinant human SDF-1a (Prospec, Israel) at 100 ng/ml was put in the lower wells of the plate, and a transwell filter was placed thereon. Subsequently, mobPBSC ($3 \times 10^5$) stained with CFSE were put on top of the transwell filter to observe, in an incubator (37° C., 5% $CO_2$), the chemotaxis of the primed mobPBSC toward SDF-1a. The results were obtained by photographing, under a 40x-magnitude microscope, at 10 different spots, the fluorescence under the transwell filter, and quantifying the primed-mobPBSC that migrated toward SDF-1a. According to the result, an increase in chemotaxis was more evident in APS-primed mobPBSC than in vehicle-primed mobPBSC (FIG. 12B).

Figure 13A:
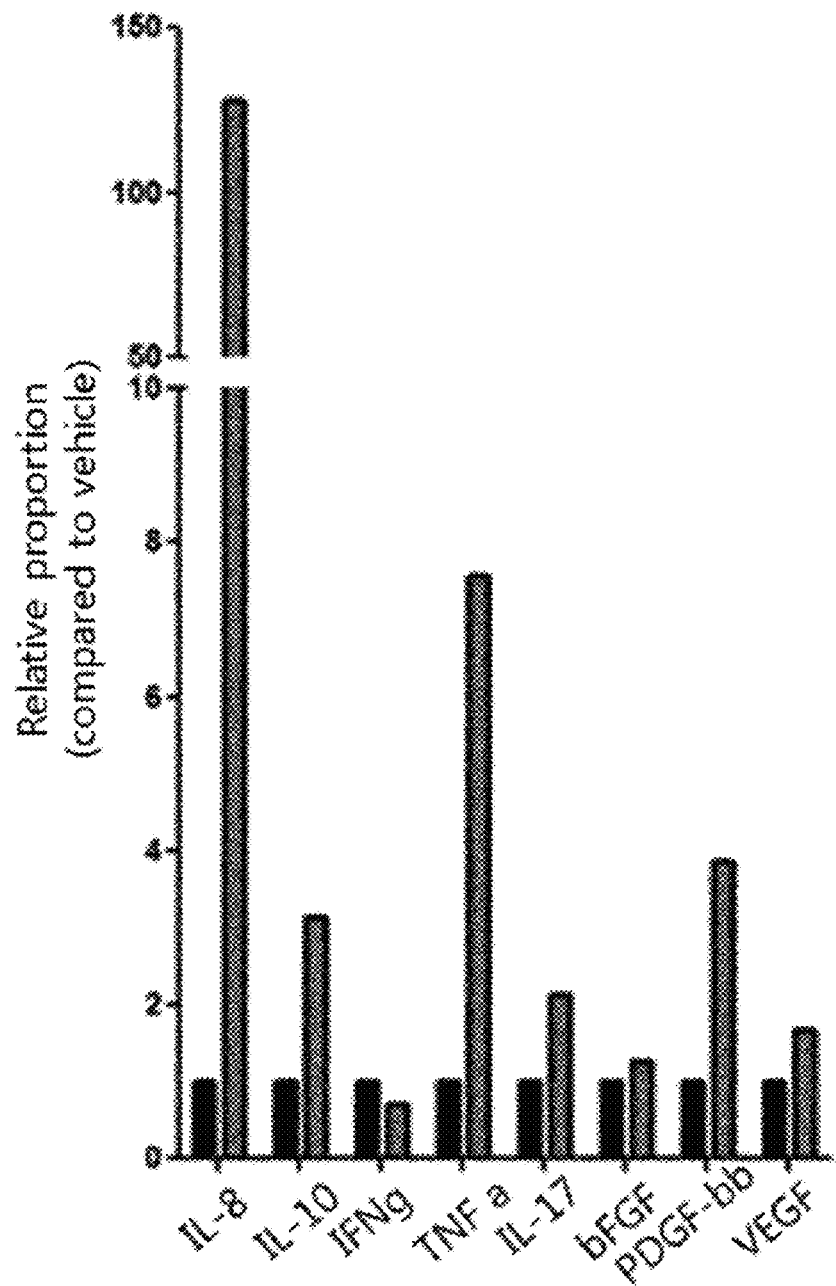
FIGS. 13a-13c show the analyzed results of ELISA with respect to the expression of IL-8, IL-10, TNF-, IL-17, PDGF and VEGF in a supernatant, in which Veh/APS-primed mobPBSC are cultured, and the analyzed results of the Matrigel tube formation and migration of HUVEC that are treated with the above supernatant.
Figure 13B:
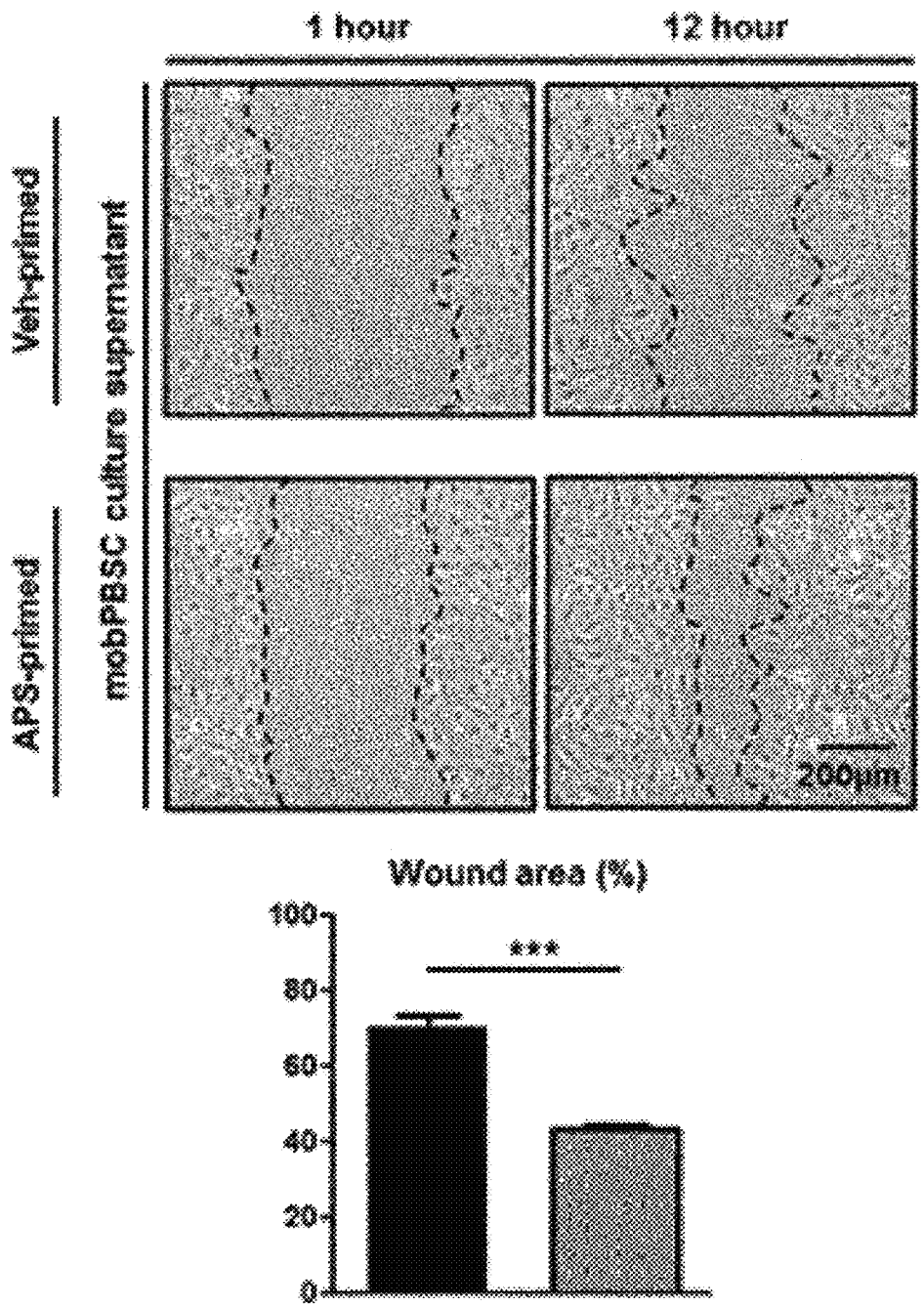
Figure 13C:
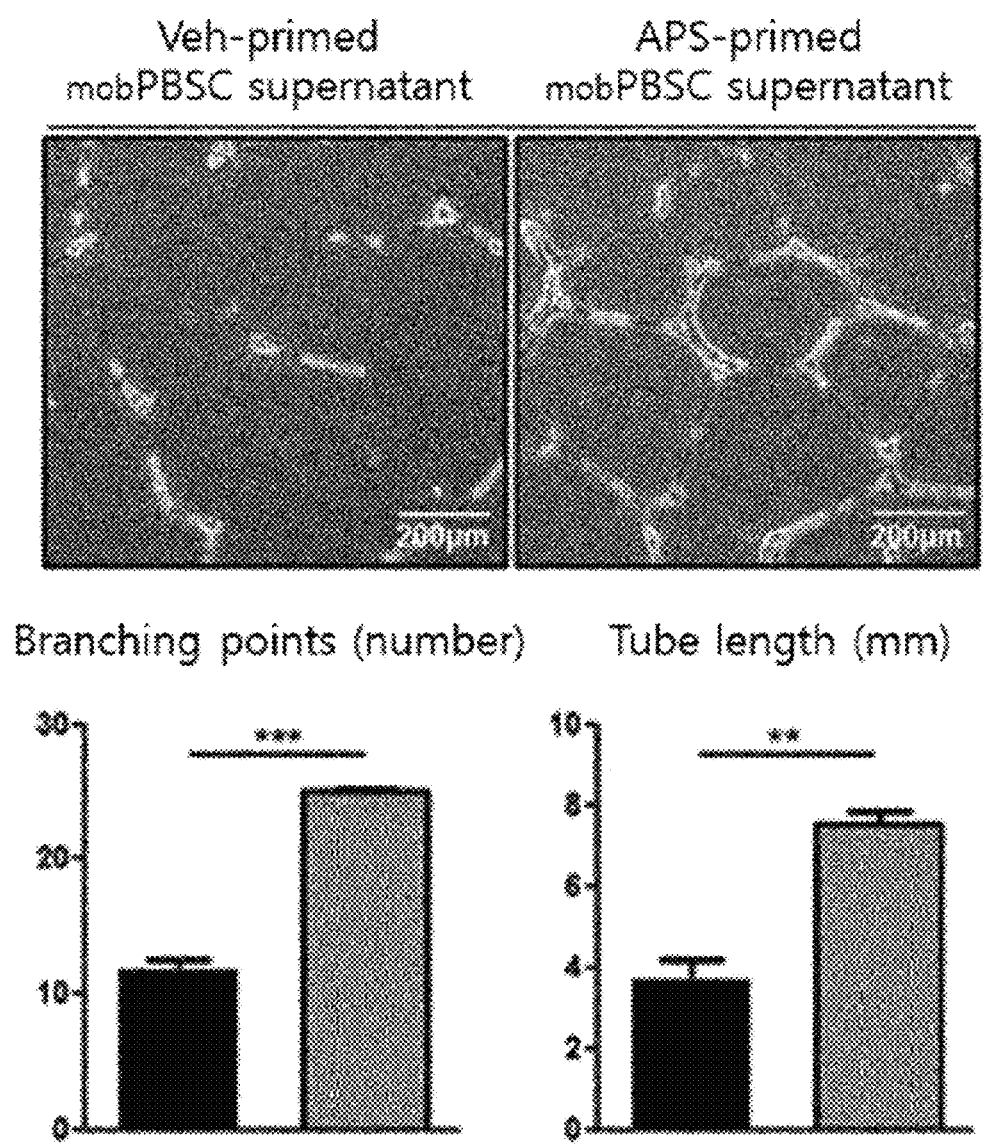

In FIG. 13, primed mobPBSC were incubated in an EBM2 (Lonza, Switzerland) culture medium that contains 5% FBS (GIBCO), and then the supernatant, in which vehicle/APS-primed mobPBSC were incubated, was stored at −20° C. until being used in the next test. ELISA (enzyme-linked immunosorbent assay) was performed by using a Bio-Plex Prot™ Array System Kit and equipment (Bio-Rad, USA) to analyze a chemokine and cytokine, such as TNF-α, IL6, IL8, IL10, IL17, IFNg, PDGF-BB VEGF and basic FGF, secreted from primed mobPBSC. According to the result, an increase in the secretion of IL-8, IL-10, TNF-α, IL-17, PDGF and VEGF was more evident in APS-primed mobPBSC than in vehicle-primed mobPBSC, and no significant change in IFN-γ, basic FGF was observed [FIG. 13A]. The analysis of the migration and Matrigel tube formation of HUVEC was conducted by using the supernatants of vehicle-primed mobPBSC and APS-primed mobPBSC. According to the result, an increase in migration [FIG. 13B] and tube formation [FIG. 13C] were more evident in HUVEC that were treated with the supernatant of APS-primed mobPBSC as compared with vehicle-primed mobPBSC.

Example 8. Identification of Effect of Vasculogenesis (In Vivo Test)

In the present example, it was proved that APS-primed mobPBSC were more effective in facilitating vasculogenesis in the pre-clinical state, as compared with the aforementioned vehicle-primed mobPBSC.

Figure 14A:
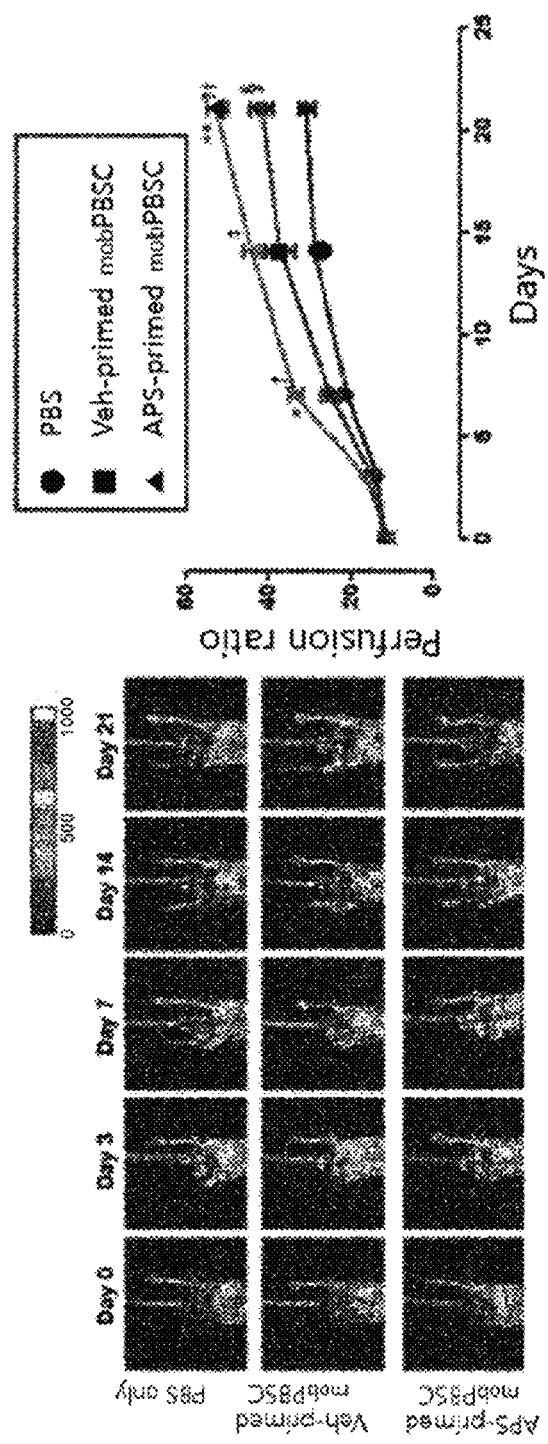
FIGS. 14a-14c show the histological analysis and measured results of the extent of perfusion after injection of Veh/APS-primed mobPBSC into an ischemic hindlimb model of an athymic nude mouse with an inhibited immune system, and also vasculogenesis by the cells into which APS-primed mobPBSC are injected.
Figure 14B:
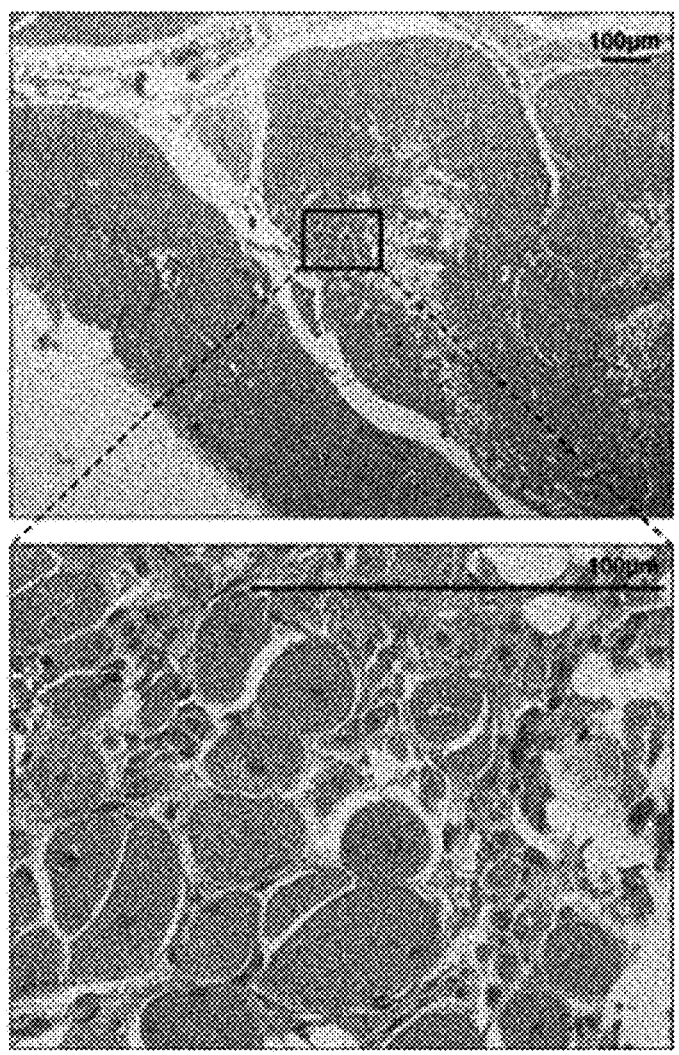
Figure 14C:
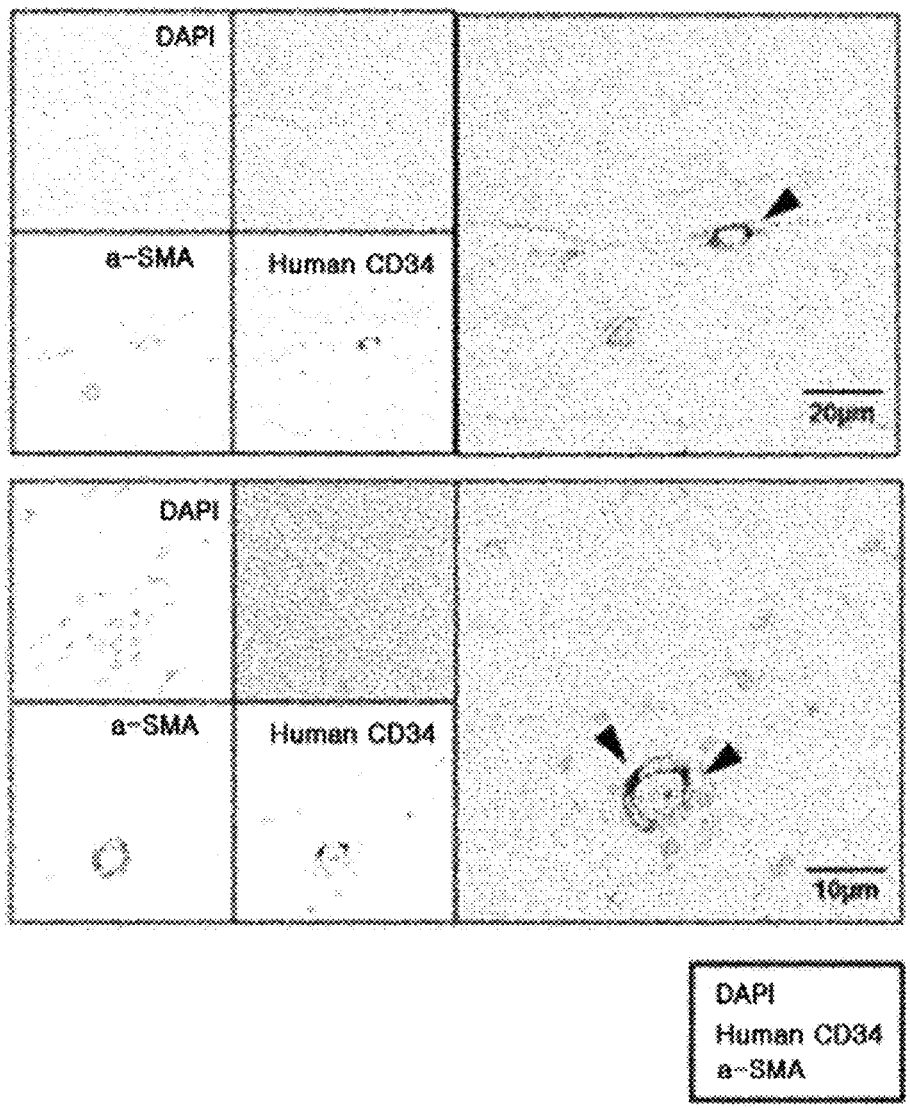

To be specific, for the examination of an in-vivo effect of mobPBSC that were primed with an APS, an ischemic hindlimb model was prepared with the hindlimb of athymic nude mice (BAL/c-nu, aged 6-8 weeks, 16-20 g, Orient Bio, Korea) with an inhibited immune system, and a Matrigel plug assay was conducted. The experimental groups and control group were, (1) a control group into which PBS was injected, (2) an experimental group into which vehicle-primed mobPBSC were injected, and (3) an experimental group into which APS-primed mobPBSC were injected, where each group contained 7 mice. For the ischemic hindlimb model, the mice were anesthetized by an intraperitoneal injection of 50 µl of ketamine and xylazine, which were mixed in the ratio of 1:4. Subsequently, the femoral artery was tied to prepare the model, and PBS and cells ($3\times10^5$/50 μl) were injected into the adductor muscle (2 sites) immediately afterward. LDPI (Moor Instruments) was performed 0, 3, 7, 14 and 21 days from the test date, and on the $21^{st}$ day, the mice were euthanized and then the hindlimbs were separated to compare the extent of tissue recovery. According to the result, as seen in FIG. 14, perfusion improved more with the APS-primed mobPBSC (n=7) than in the group into which PBS (n=7) or vehicle-primed mobPBSC (n=7) was injected [FIG. 14A]. In addition, each experimental group was stained with H&E for the histological investigation of ischemic tissues [FIG. 14B]. Also, to observe the newly-formed and mature blood vessels, muscle tissues were stained with an anti-alpha smooth-muscle actin (SMA-α, Sigma-Aldrich, USA). Next, the mice tissues were examined for human-derived cells by immunofluorescence staining of anti-human CD34 (Leica Biosystems, Germany) and DAPI. The results were analyzed by a confocal or fluorescence microscope. As the result of immunofluorescence staining by using an antibody that is specific to human cells for CD34 (cluster of differentiation 34, green color), which is a vascular endothelial cell primer, and SMA-α (red color), it was identified that the cells into which APS-primed mobPBSC were injected actually exhibit vasculogenesis (FIG. 14C).

Figure 15:
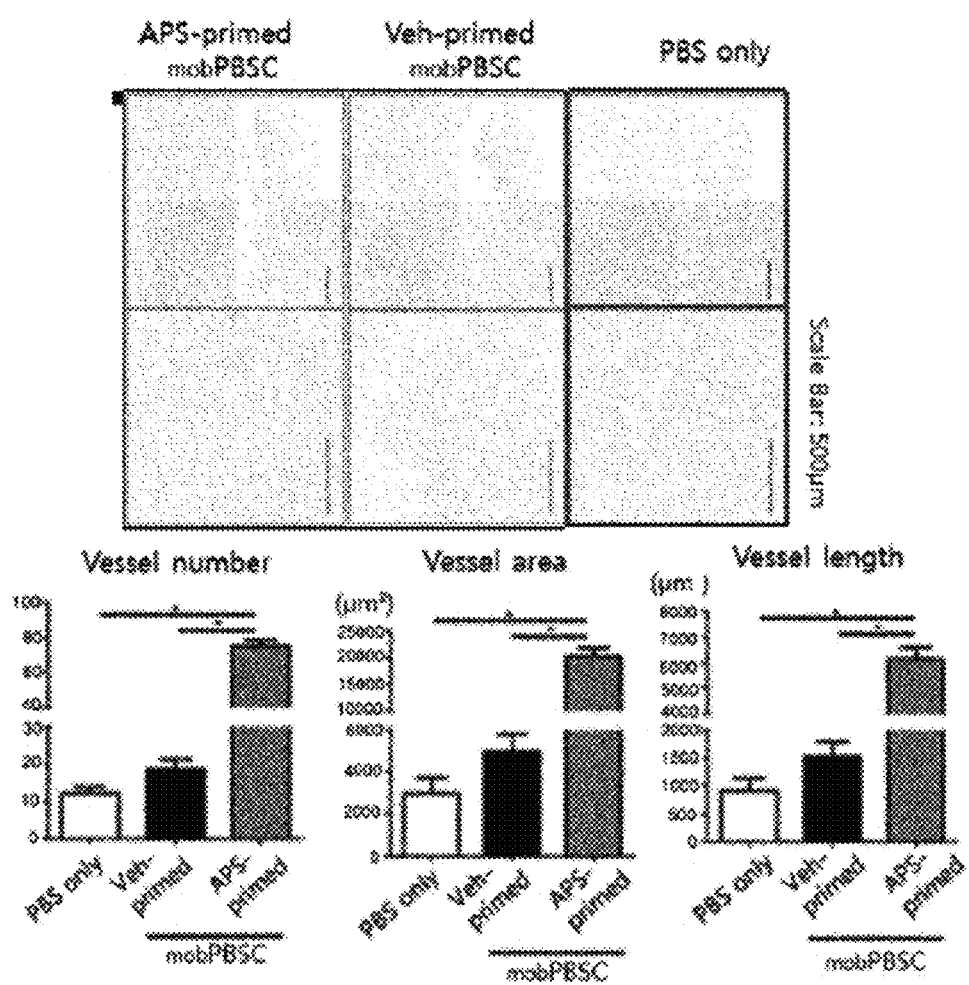
FIG. 15 shows that vasculogenesis is facilitated more in the group in which APS-primed mobPBSC are injected into an ischemic hindlimb model of an athymic nude mouse with an inhibited immune system than in the control group.

Moreover, as the result of staining with SMA-α (red color) to observe blood vessels, it was identified that more blood vessels were formed when APS-primed mobPBSC were injected, as seen in FIG. 15. Upon quantification, it was identified from the results that the number of blood vessels, area of blood vessels and length of blood vessels significantly increased when APS-primed mobPBSC were injected, as compared with the groups with PBS or vehicle-primed mobPBSC.

Figure 16A:
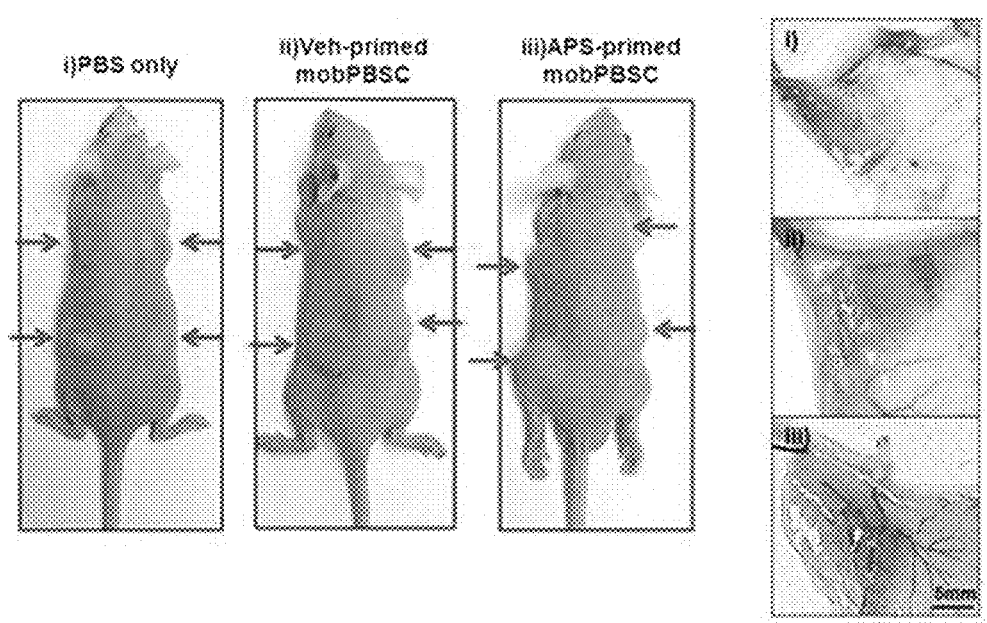
FIGS. 16a and 16b are the result of injecting Matrigel into nude mice with an inhibited immune system to compare the properties of blood vessel formation in the surroundings, and show that excellent properties of blood vessel formation are observed upon injection of mobPBSC (mobilized by G-CSF and APS-primed), as compared with the control group.
Figure 16B:
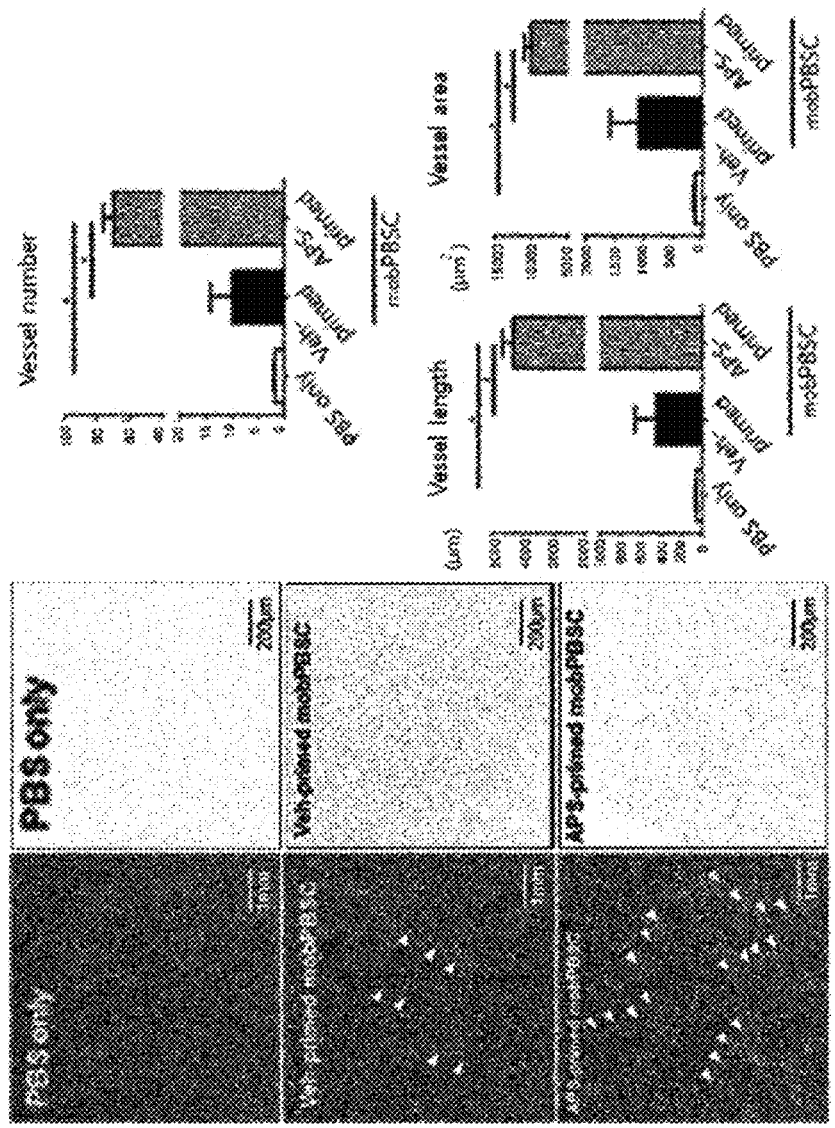

FIG. 16 relates to the Matrigel plug assay, where 350 μl of cold Matrigel (BD bioscience), to which VEGF-A (1 μg/ml), b-FGF (1 μg/ml) and vehicle/APS-primed mob-PBSC ($5\times10^5$ cells) were added, was subcutaneously injected into the mice. Matrigel that does not contain cells was injected into the control group. The mice were euthanized on the $21^{st}$ day from the test date, and then the Matrigel was separated. H&E and immunofluorescence staining was conducted for the comparison of blood vessel formation. Vasculogenesis was observed in a round shape that contains a linear structure and red blood cells. All animal testing was conducted upon approval of the Institutional Animal Care and Use Committee of Clinical Medicine Center of the Seoul National University and in accordance with the guidelines of the International Research Fellow of the Laboratory Animal Care and Use. According to the result, more blood vessels were observed with the naked eye when APS-primed mobPBSC were injected, as compared with the groups into which PBS or vehicle-primed mobPBSC were injected (FIG. 16A). In addition, according to the results of H&E staining and SMA-α (red color) staining, more blood vessels were actually observed when APS-primed mobPBSC were injected; upon quantification, it was identified from the results that the number, area and length of blood vessels significantly increased when APS-primed mobPBSC were injected, as compared with the groups into which PBS or vehicle-primed mobPBSC were injected (FIG. 16B).

Photographs in the drawings were obtained by an Olympus IX2 inverted fluorescence microscope (Olympus), Olympus DP50 CF CCD camera and analysis 5.0 software, and confocal photographic results were obtained by a Zeiss LSM-710 META confocal microscope (Olympus) and ZEN 2009 analysis software.

Example 9. Stability Test of APS (Thrombogenicity Test)

In the present example, APS stability was evaluated by a thrombogenicity test. Platelets have a significant impact on the recovery of damaged tissues but also contributes to thrombogenicity. The risk of increased blood clots prior to tissue damage is a reason for using an APS for a disease, such as ischemic cardiovascular disease, whose pathogenesis is 'thrombogenicity'.

Figure 17A:
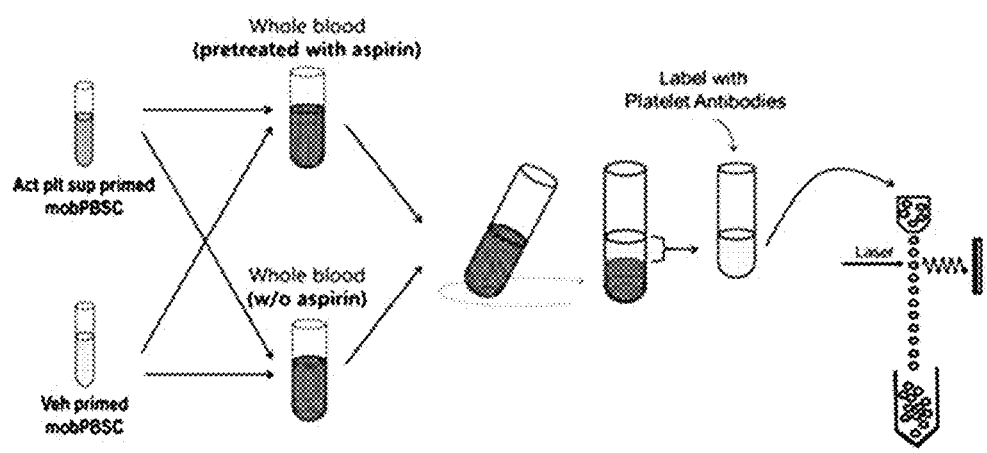
FIGS. 17a and 17b show a secured stability of an APS.

FIGS. 17A and B show the results of a thrombogenicity test of APS-primed mobPBSC to identify the stability of an APS. During the present test, mobPBSC were added to blood, and then the degree of activation of platelets were measured. FIG. 17A schematically illustrates the process of identifying the activation of platelets by CD41 (integrin alpha-IIb chain) and CD61 (integrin beta-3 chain), both of which are two glycoproteins present in the platelet membrane.

In order to apply the clinical conditions of APS-primed mobPBSC injection into the coronary artery of a patient, vehicle/APS-primed mobPBSC were mixed in the blood at a concentration of $1\times10^7$ cells/ml, and then a control group (without aspirin) and an experimental group(s) (containing aspirin at 20 μg/ml) were prepared in separate sodium citrate test tubes (BD-Plymouth, UK). After activating platelets by mixing thoroughly for 30 minutes, centrifugation was performed at 130×g for 20 minutes to separate PRP. The PRP obtained as such was stained with FITC fluorescence-labeled CD41 and CD61 antibodies and, with the use of an antibody of FITC fluorescence-labeled lgG, set as the control group. It was protected from strong impact to prevent self-regulated activation of platelets during separation and staining.

Figure 17B:
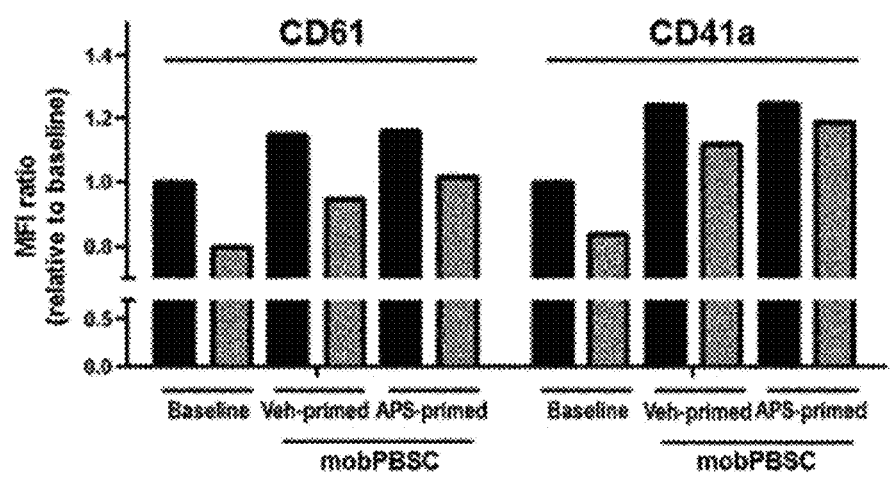

FIG. 17B shows the results of FACS analysis. Both CD61 and CD41a exhibit an increased FACS result upon activation of platelets. As a result, all of the platelets in the whole blood to which APS- and vehicle-primed mobPBSCs were mixed exhibited increased activity. However, the platelet response was observed to decrease by aspirin, which is an antiplatelet formulation used in cardiovascular patients.

It was discovered from such results that the platelet activity of whole blood partly increased due to APS-priming, which again decreased due to a simultaneous use of an antiplatelet formulation. In other words, the drawing suggests that the use of an antiplatelet formulation can reduce the risk of blood clotting in APS-priming and thus resolve the stability problem.

All statistical analyses were conducted by a Prism 5.0 program (GraphPad Software, USA) and SPSS Version 18 (SPSS Inc., USA). The results were shown as the average of average±standard deviation. The experimental groups were compared to one another by conducting post hoc comparison, such as a Bonferroni analysis and unpaired t-test, and analyzing the gap. A p-value of <0.05 was understood to show a statistical significance.

Above description of the present invention is for purposes of illustration, and it will be understood by those with ordinary skill in the technical field, to which the present invention belongs, that variations to other specific forms are possible without changing the technical spirit or essential features of the present invention. Therefore, it should be understood that the examples described above are intended to be illustrative and as non-limiting in all aspects.

The invention claimed is:

1. A method comprising:
   collecting peripheral blood from a subject who has been pre-treated with a cytokine;
   collecting mononuclear cells from the peripheral blood;
   subsequent to collecting mononuclear cells, priming at least a part of the collected mononuclear cells with at least one priming agent selected from erythropoietin (EPO) and activated platelet supernatant (APS) under appropriate conditions to provide in-vitro-primed mononuclear blood stem cells having improved blood vessel formation properties; and
   subsequent to priming, administering a composition comprising the in-vitro-primed mononuclear blood stem cells to a person such that the composition contacts the person's tissue having an ischemic condition.

2. The method of claim 1, further comprising:
   treating the subject with the cytokine for 1 day to 5 days prior to blood collecting.

3. The method of claim 1, wherein the cytokine is granulocyte colony stimulating factor (G-CSF).

4. The method of claim 1, wherein the tissue having the ischemic condition comprises that of muscle, brain, heart, kidney or large intestine.

5. The method of claim 1, wherein the person has a symptom or disease caused by the ischemic condition in the tissues, wherein the symptom or disease is selected from the group consisting of cerebral infarction, stroke, reperfusion injury, myocardial infarction, congestive heart failure, peripheral vascular obstruction, cardiac hypertrophy, low heart contraction, low heart dilatation, maladaptive cardiomegaly, systolic heart failure, diastolic heart failure, hypertensive heart failure, artery or mitral valve diseases, heart blood vessels with pulmonary valve diseases, and ischemic heart blood vessels.

6. The method of claim 1, wherein the person is the subject.

7. The method of claim 1, wherein the person is not the subject.

8. The method of claim 1, wherein the tissue having the ischemic condition comprises a heart tissue, wherein the patient has a heart disease caused by the ischemic condition, wherein the heart disease is at least one selected from the group consisting of myocardial infarction, angina, congestive heart failure, cardiac hypertrophy, low heart contraction, low heart dilatation, maladaptive cardiomegaly, systolic heart failure, diastolic heart failure, and hypertensive heart failure.

9. The method of claim 1, wherein priming under appropriate conditions comprises priming in a culture fluid containing the at least one of priming agent selected from EPO and APS at a density of $3 \times 10^7$ cells/ml or higher.

10. The method of claim 1, wherein priming under appropriate conditions comprises priming in a culture fluid containing the at least one of priming agent selected from EPO and APS for 6 hours while stirring in an incubator to which $CO_2$ is supplied.

11. The method of claim 1, wherein priming under appropriate conditions comprises priming in a culture fluid containing the at least one of priming agent selected from EPO and APS while stirring.

12. The method of claim 1, wherein priming under appropriate conditions comprises priming in an incubator to which $CO_2$ is supplied.

13. The method of claim 1, wherein priming under appropriate conditions comprises priming in a culture fluid containing the at least one of priming agent selected from EPO and APS.

\* \* \* \* \*